United States Patent [19]
Sasamoto et al.

[11] Patent Number: 5,262,526
[45] Date of Patent: Nov. 16, 1993

[54] FLUORESCENT COMPOUND, COMPLEX, REAGENT, AND SPECIFIC BINDING ASSAY EMPLOYING SAID REAGENT

[75] Inventors: Kazumi Sasamoto; Daikichi Horiguchi, both of Kumamoto; Masahiro Nobuhara; Hiroshi Mochizuki, both of Tokyo, all of Japan

[73] Assignees: Dojindo Laboratories, Kumamoto; Mochida Pharmaceutical Co., Ltd., Tokyo, both of Japan

[21] Appl. No.: 811,533

[22] Filed: Dec. 20, 1991

[30] Foreign Application Priority Data

Dec. 21, 1990 [JP] Japan .................. 2-405268
Mar. 1, 1991 [JP] Japan .................. 3-036020

[51] Int. Cl.$^5$ ............... C07D 257/10; C07H 19/073; C09D 29/036
[52] U.S. Cl. .................. 534/551; 534/560; 534/561; 534/643; 534/653; 534/657; 534/702; 534/727; 536/25.32; 530/406; 540/3; 540/472; 540/465
[58] Field of Search .............. 540/472, 465.3, 107, 540/111; 534/551, 561, 657, 727, 643, 702, 653, 560; 530/406; 536/25.32

[56] References Cited

U.S. PATENT DOCUMENTS

4,927,923  5/1990  Mathias et al. .............. 540/472

FOREIGN PATENT DOCUMENTS

0180492   5/1986  European Pat. Off. ........... 540/472
62-188687 6/1976  Japan .
57-186170 4/1982  Japan .
60-500767 3/1984  Japan .
64-47952  11/1989 Japan .................. 530/405

OTHER PUBLICATIONS

Chandler, et al., J. Heterocyclic Chem. 18 599 (1981).

(List continued on next page.)

Primary Examiner—Mukund J. Shah
Assistant Examiner—E. C. Ward

[57] ABSTRACT

A fluorescent compound, which is readily capable of forming a stable complex with a rare-earth metal ion having fluorescence with satisfactory intensity even in an aqueous system and long fluorescence lifetime when formed a complex with the rare-earth metal ion, a complex of the fluorescent compound and the rare-earth metal ion, and a labelled reagent made therefrom, together with a specific binding assay using said labelling agent.

A fluorescent compound expressed by the following formula A, typically exemplified by 2,15-diaza[3,3](2,9)-1,10-phenanthrolinophane-$N^2,N^{15}$-diacetic acid.

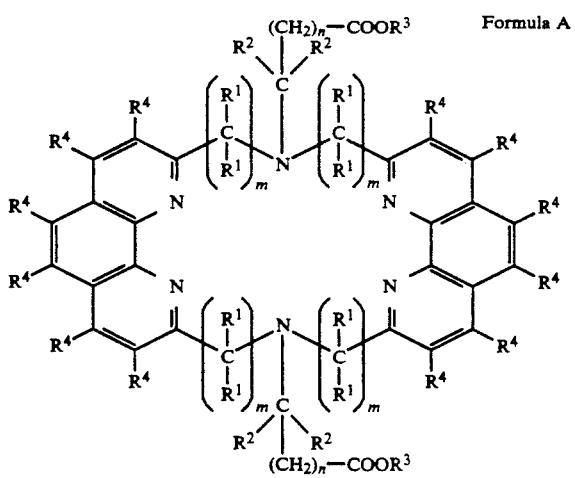

13 Claims, 17 Drawing Sheets

OTHER PUBLICATIONS

Alpha et al., Angew. Chem. Int. Ed. 26(3) 1987, 266-267.

Huang et al., Nippon Kagaku Kaishil 66-73, 1981.

K. C. Joshi et al, *Journal of Fluorine Chemistry*, vol. 13, pp. 261-265, 1979.

S. E. Livingstone et al, *Aust. J. Chem.*, vol. 29, pp. 1845-1850, 1976.

H. Nakatani et al., *The Review of Physical Chemistry of Japan*, vol. 42, No. 2, pp. 103-107, 1972.

E. P. Diamandis et al, *Journal of Immunological Methods*, vol. 112, pp. 43-52, 1988.

G. Blasse, *Chemistry of Materials*, vol. 1, pp. 294-301, 1989.

S. J. Keipert, C.B. Knobler & D. J. Cram, Host-Guest Complexation, 43, Synthesis and Binding Properties of a Macrocycle Composed of Two Phenanthrolines and Two Slfonamide Units, Tetrahedron, vol. 43, No. 21, pp. 4861-4874, 1987.

M. A. Chan, A. C. Bellem & E. P. Diamandis, Time-Resolved Immunofluorometric Assay of Alpha-Fetoprotein in Serum and Amniotic Fluid, with a Novel Detection System, Clinical Chemistry, vol. 33, No. 11, pp. 2000-2003, 1987.

a: using labelled antibody prepared in Ex. 9(1)
b: using labelled antibody prepared in Ex. 9(2)
c: using labelled antibody prepared in Ex. 9(3)

a: fluorescent compound (p)-labelled antibody
b: fluorescent compound (γ)-labelled antibody
c: fluorescent compound (v)-labelled antibody a: compound (v)-labelled antibody in Ex.16
b: biotin-streptavidin system in Ex. 21
c: antibody conjugated to BSA labelled with compound (v) in Ex. 22

5,262,526

FLUORESCENT COMPOUND, COMPLEX, REAGENT, AND SPECIFIC BINDING ASSAY EMPLOYING SAID REAGENT

INDUSTRIAL FIELD

This invention concerns a novel fluorescent compound useful for fluorescent assay, a complex comprising said fluorescent compound as ligand, a reagent bearing said fluorescent compound, and a specific binding assay by using said reagent and measuring fluorescence intensity by means of the fluorescence analysis, especially the time-resolved fluorescence analysis.

BACKGROUND OF THE INVENTION

As for qualitative or quantitative measurement of a target substance in biological sample, technique employing the substance capable of competing or specifically binding with said target substance, with which a labelling agent having particular signal is bonded, has been so far known widely. Particularly, the assay based on the antigen-antibody reaction or hybridization of nucleic acid is very useful, since the assay permits measurement of said target substance with high sensitivity.

These assays permit to measure the presence or absence of the target substance or either its amount or concentration by binding a substance, to which the labelling agent had been bonded, directly or indirectly with the target substance, and by competing a substance or its derivative, to which the labelling agent had been bonded, with the target substance, followed by measuring signal intensity emitted from the label.

As one of the labelling agent for such uses, radioactive isotopes have been known and their uses have permitted to detect the target substance with high sensitivity. Radioactive isotopes, however, possess a large disadvantage that their storage, use, and disposition, accompany danger, so that in recent years, the use of non-radioactive labelling agents instead of radioactive isotopes has increased rapidly.

As a typical non-radioactive labelling agent, enzyme has been known. Particularly, the method employing enzymes as the labelling agent has found wide use in immunoassay. Some significant problems, however, exist in the use of enzymes as the labelling agents.

Namely, it can be cited that reproducibility of the results of assay using enzyme as the labelling agent are low due to the fact that enzyme is readily affected by several conditions such as temperature, sample's characteristics, that the enzymes commercially available are generally expensive, etc.. It can be also cited that, in the immunoassay, enzyme is bonded with the specific binding agent which binds specifically or competes with the target substance, but, as a fatal fault, the activities of both enzyme and specific binding agent are reduced as a result of bonding the enzyme to the specific binding agent.

Fluorescent substance is a one of the candidates of a non-radioactive labelling agent other than enzyme. As fluorescent substances so far employed as the labelling agent, fluorescein, rhodamine, dansyl chloride, umbelliferone, etc. are known.

The measurement method using fluorescent substance as the labelling agent takes advantage of fluorescence phenomenon, i.e. the phenomenon that certain compound, when receiving certain exciting light, emits proper light based on the electronic configuration of said compound, and in principle high sensitivity can be expected in this method. The use of fluorescent substance as the labelling agent, however, raises some problems.

One of said problems is the high background noise caused by Rayleigh scattering. Furthermore, as for measurement of the target substance in biological samples such as serum and urine, another problem is that a number of fluorescences derived from substances in biological samples seriously disturb detection of the fluorescence derived from said labelling agent.

These problems are primarily due to the fact that fluorescent substances so far employed generally have small Stokes shifts, and the particular property to distinguish the fluorescence derived from the labelling agent from the background fluorescence does not exist. Providing that such problems are dissolved, use of fluorescent substance as the labelling agent will become a very useful means in the field of analysis.

It has been found in recent years that complex formed from certain ligand and rare-earth metal ion emits strong fluorescence, wherein exciting light is absorbed by the ligand and the energy is transferred from the excited triplet state of the ligand to the rare-earth metal ion, so that fluorescence based on transition of the f orbital electron of said rare-earth metal ion is observed. As rare-earth metal, europium, terbium, samarium, etc., are exemplified, these rare-earth metals themselves possess intrinsic fluorescences.

In such complex, exciting wavelength depends upon the kind of ligand and emission wavelength depends upon the kind of rare-earth metal. And, such fluorescence derived from complex have at least 100 nm or more of Stokes shift and also possesses much longer fluorescence lifetime of the order above 1 $\mu$s compared with the background fluorescences derived from protein and others with fluorescence lifetime of about 10 ns. Accordingly, taking these advantages, it is possible to distinguish the fluorescence derived from said complex completely from other background fluorescences, so that the fluorescent complex bearing rare-earth metal ion becomes favorable as the labelling agent.

Some of the compounds forming complex with rare-earth metal ion are well known already.

As one of these, $\beta$-diketone forming complex with europium ion or samarium ion can be cited.

As regards the complex, various properties are reported, including that $\beta$-diketone is a divalent ligand and more than 3 molecules or more of this ligand usually coordinate with europium ion (Krishna C. Joshi et al., Journal of Fluorine Chemistry, 13, 261–265 (1979); Livingstone S. E. et al., Aust. J. Chem., 29, 1,845–1,850 (1976); H. Hang et al., Nippon Kagaku Kaishi, 1, 66–73 (1981), etc.)

As an example employing such complex as the labelling agent, a description as to the antibody, to which the complex formed from $\beta$-diketone and europium ion or terubium ion is bonded, is found in Japanese Patent Publication (1987) 62-18868.

However the stability of the complex of $\beta$-diketone and a rare-earth metal ion is so low that, under practical assay conditions, the complex can not be maintained throughout the assay period. So it is very difficult to use the complex as the labelling agent in the immunoassay and others.

A number of reports as to the complex formed from rare-earth metal ion and ethylenediamine tetraacetic acid (EDTA) including that by Nakatani H. et al. (The Review of Physical Chemistry of Japan, 42, 103-107 (1972)) are also found.

As an example using such complex as the labelling agent, a description as to EDTA derivative which coordinates lanthanide ion strongly and has the functional group, being capable of binding the complex to antigen or antibody, is found in Japanese Patent Application Kokai (1985) 60-500767.

Complex of EDTA and rare-earth metal ion has the excellent stability of the complex itself, but has a fatal fault that fluorescence enhancing property due to the complex formation is lacking. Namely, EDTA lacks the ability to absorb and transfer energy and the fluorescence intensity derived from the complex of EDTA and said rare-earth metal ion is very small. So, the complex of EDTA and rare-earth metal ion has a similar fault in the use of the preceding fluorescent substance so far employed.

In Japanese Patent Application Kokai (1982) 57-186170, E. Soini, Hemmile, and others revealed a method enhancing the fluorescence intensity by allowing metal ion to transfer between two kinds of complex-forming compound consisting of non-fluorescent and fluorescent compounds. Concretely, the complex of EDTA analogue and metal ion, which is highly stable but non-fluorescent, is employed as the labelling agent in specific binding reaction. After the reaction, detergent and complex-forming compounds are added to transfer the metal ion from the complex of EDTA analogue to the complex-forming compounds, resulting the formation of new fluorescent complex in liquid phase.

The crucial fault of the method by Soini, Hemmile, and others lies in a high possibility that, due to the transfer of metal ion between two kinds of complex-forming compound, another metal ion expected not to participate in this reaction system participates in the reaction system, i.e. that contamination takes place. Accordingly, the close attention must be paid in measurement not only to reagent and equipment but also to all apparatuses to be employed and experimental environment, in order to prevent contamination by metal ion from the outside.

As more improved fluorescent compound, 4,7-bis(-chlorosulfophenyl)-1,10-phenanthroline-2,9-dicarboxylic acid was reported by Diamandis E. P. and others (Clin. Chem., 33, 2000 (1987); Journal of Immunological Methods, 112, 43 (1988)). In Japanese Patent Application Kokai (1989) 64-47952, a method for bonding the bovine serum albumin (BSA) labelled with the fluorescent compound to antibody and a method for binding, via avidin-biotin reaction, the avidin labelled with said fluorescent compound to the antibody labelled with biotin, i.e. method with the intervention of intermediate, were described.

The feature of said fluorescent compound by Diamandis and others lies in that the compound coordinates rare-earth metal ion at the nitrogen atom site of the phenanthroline ring and forms the bond with the amino group of protein by its sulfonylchloride group. The stability of the complex formed from the compound and rare-earth metal ion is lower than expected. Furthermore, the compound is not designed so as to be insensitive to aqueous quenching of fluorescence, which often encountered in the measurement of fluorescence in aqueous solvents, although this is understandable considering the steric structure.

Hence, in the use of the fluorescent compound, such problems result, as that, throughout or after the immunological reaction, a large excess of metal ion must be added and that the solid phase to which an antibody is immobilized must be dried before measurement of fluorescence. Furthermore, another problem results that the fluorescence intensity emitted by the complex formed from the fluorescent compound and rare-earth metal ion is not so strong as expected, so that, as was indicated in preceding Japanese Patent Application Kokai (1989) 64-47952, the sensitivity is not high enough for the practical use, unless proteins such as BSA and avidin intervene between the antibody as specific binding agent and the fluorescent compound to increase the number of label per an antibody molecule.

Alpha B. et al. and Blasse G. reported on the fluorescence emitted by the complex formed from cryptand and rare-earth metal ion (Angew. Chem. Int. Ed. Engl., 26, 266-267 (1987); Chemistry of Materials, 1, 294-301 (1989)).

Cryptand is comparatively favorable for the stability and the fluorescent property when used as complex. It has a problem, however, that introduction of a functional group for bonding to protein into its parent structure is difficult. Another problem is arisen from the fact that the process of said complex formation, i.e. chelating process, requires the reaction at high temperature for a prolonged time, although once metal ion is incorporated into the center of the basic structure of cryptand, the formed complex becomes stable.

As the large-ring compound capable of forming chelate, other than the well known preceding compound, compounds such as crown ether and large-ring polyamine are known.

Although these compounds with large-ring structure have the possibility to form comparatively stable complex with metal ion, they require that the cavity size of the ring must fit the ion radius of the metal to coordinate, so that possible combinations of the metal ion with the compound having ring structure are remarkably limited. It is supposed further that the complex of bipyridine, large-ring polyamine, or others is less stable than the complex using, as ligand, EDTA or others permitting the three-dimensional coordination, since the former having a comparatively planar structure can coordinate the metal ion only two-dimensionally.

As described above, the utilization of fluorescent substance as the labelling agent for measurement of the target substance in biological sample is considered to be very useful, although accompanied with subjects to be solved.

The solution of aforementioned subjects is achieved by the development of the fluorescent substance, which is stable, has a large Stokes shift and a long fluorescence lifetime, and is very liable to quenching even in aqueous solvent.

SUMMARY OF THE INVENTION

This invention has been devised taking such situation into consideration. Its object is to offer a fluorescent compound, which is readily capable of forming a stable complex with rare-earth metal ion, having fluorescence with satisfactory intensity even in aqueous system and long fluorescence lifetime when formed a complex with said rare-earth metal ion, a complex of said fluorescent compound and rare-earth metal ion, and a reagent composed of specific binding agent and said fluorescent compound or said complex, which is bonded either directly or indirectly with said specific binding agent, together with offer of a specific binding assay using said labelled reagent.

"Specific binding agent" in this specification means the substance binding specifically with a certain substance.

As the result of vigorous studies to solve aforementioned various problems encountered in the technics so far employed, the inventors have completed this invention by successfully developing the novel fluorescent compound which is very useful in the application to the fluorescent assays, particularly the time-resolved fluorescent assays, and also usable by binding with specific binding agent, together with successful development of the specific binding assay as its concrete application.

Namely, a 1st aspect of this invention is the fluorescent compound expressed by the following formula A.

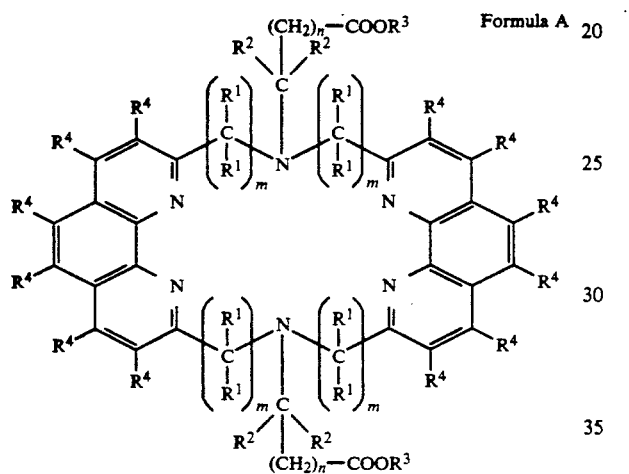

wherein m represents 1 or 2, n represents an integer selected from the group consisting of 0, 1, 2, 3 and 4;

$R^1$ is independently selected from the group consisting of hydrogen atom, an alkyl group, an alkenyl group, an alkynyl group, an aralkyl group, and an aryl group;

$R^2$ is independently selected from the group consisting of hydrogen atom, an aryl group, and an alkyl group;

$R^3$ is a functional group represented by $-R^{3-1}-R^{3-2}$, wherein $R^{3-1}$, although its presence is not indispensable, is independently selected from the group consisting of an alkylene group, an arylene group, and an aralkylene group, and $R^{3-2}$ is indispensable and independently selected from the group consisting of hydrogen atom, an alkyl group, an aryl group, carboxyl group, hydroxyl group, an alkoxyl group, an amino group, an amide group, sulfonamide group, sulfide group, sulfoxide group, sulfone group, a halogen atom, carbonyl group, and nitro group; and $R^4$ is independently selected from the group consisting of hydrogen atom, an alkyl group, an alkenyl group, an alkynyl group, an aryl group, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group represented by $-R^{4-1}-R^{4-2}$, wherein $R^{4-1}$, although its presence is not indispensable, is independently selected from the group consisting of an alkylene group, an alkenylene group, an arylene group, and an aralkylene group, and $R^{4-2}$ is indispensable and independently selected from functional groups:

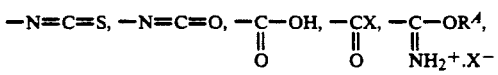

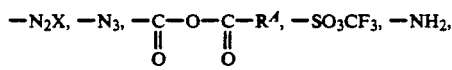

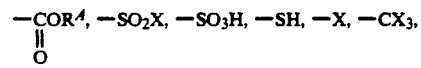

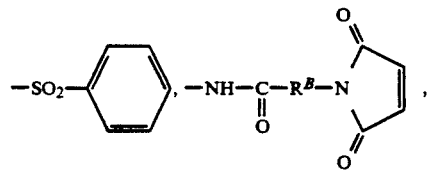

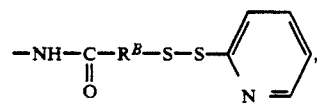

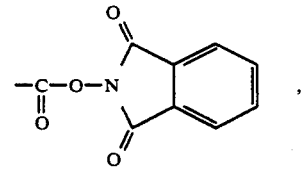

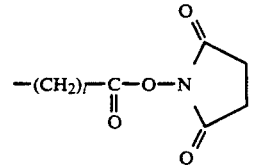

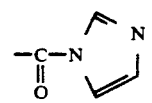

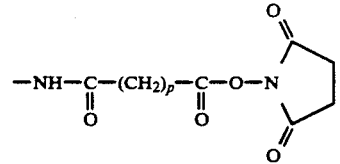

wherein X is selected from the group consisting of a halogen atom, $-OSO_3CH_3$, $-OSO_2F$, $-OSO_2CF_3$, $-SO_2C_4F_9$, and

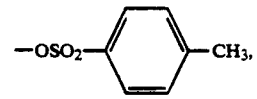

$R^A$ is selected from the group consisting of an alkyl group, an alkenyl group, an aryl group, and aralkyl group, $R^B$ is selected from the group consisting of an alkylene group, an alkenylene group, an arylene group, and an aralkylene group, and l represents an integer of from 0 to 5, p represents an integer of from 2 to 10; and wherein, R[4] may optionally take a form of either at least one aromatic ring or at least one heterocyclic ring including two or three carbon atoms which are the part of a phenanthroline ring as a result of the ring-forming condensation brought about by the bonding of neighboring R[4] to each other.

A 2nd aspect of this invention is a complex comprising the fluorescent compound constituting the 1st aspect of this invention and a rare-earth metal ion.

A 3rd aspect of this invention is the reagent comprising a specific binding agent and the fluorescent compound constituting the 1st aspect of this invention or the complex constituting the 2nd aspect of this invention bonded directly or indirectly to said specific binding agent.

In addition, a 4th aspect of this invention is a specific binding assay for a target substance in liquid sample, characterized by using the reagent constituting the 3rd aspect of this invention comprising a specific binding agent and the fluorescent compound constituting the 1st aspect of this invention bonded directly or indirectly with the specific binding agent, forming the complex of the fluorescent compound in the reagent and a rare-earth metal ion, exciting said complex, and measuring the fluorescence intensity with a long decay time emitted from the complex correlating to the amount or concentration of preceding the target substance.

A 5th aspect of this invention is a specific binding assay for a target substance in liquid sample, characterized by using the reagent constituting the 3rd aspect of this invention composed of a specific binding agent and the complex constituting the 2nd aspect of this invention bonded directly or indirectly with the specific binding agent, exciting the complex composed of the fluorescent compound and the rare-earth metal ion in said reagent, and measuring the fluorescence intensity with a long decay time emitted from said complex correlating to the amount or concentration of preceding the target substance.

DETAILED DESCRIPTION OF THE INVENTION

Figure 1:
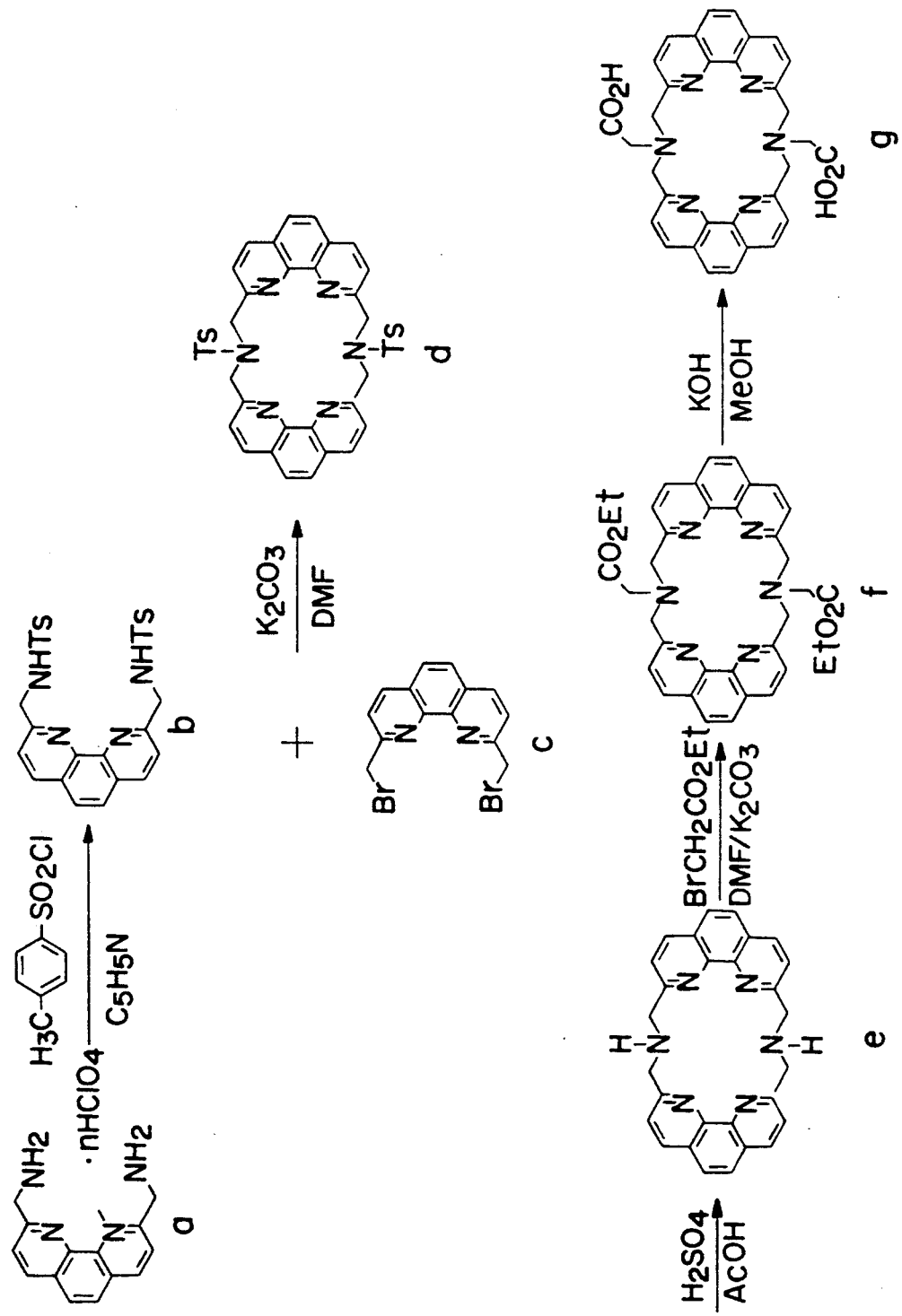
FIG. 1: The synthetic route of 2,15-diaza[3,3](2,9)-1,10-phenanthrolinophane-$N^2,N^{15}$-diacetic acid described in Example 1.

Details of the constitution of this invention are described below.

The fluorescent compound constituting the 1st aspect of this invention is expressed by the preceding formula A.

Wherein "fluorescent compound" is defined as the compound capable of enhancing the fluorescence emitted from rare-earth metal ion, when complex is formed by the coordination to the rare-earth metal ion described later.

The fluorescent compound constituting the 1st aspect of this invention expressed by the preceding formula A is characterized by that the unsared electron pair of the nitrogen atom at the central site of the ring structure of said compound coordinates the rare-earth metal ion described later and that the cavity size of the ring structure almost fits the radius of said rare-earth metal ion. Accordingly, said compound allows the stable coordination of said rare-earth metal ion.

It is also possible to provide the fluorescent compound constituting the 1st aspect of this invention with various characteristics described later, by the selection of the atom or functional group expressed by $R^1$ to $R^4$ in preceding formula A, or the selection of m and/or n.

That is $R^1$ affects the cavity size of the ring structure, the readiness for incorporating the rare-earth metal ion, the stability of complex, and others, and is independently selected from the group consisting of hydrogen atom, an alkyl group, an alkenyl group, an alkynyl group, an aralkyl group, and an aryl group. The selection of hydrogen atom is favorable, since the ring structure becomes flexible and the cavity size fits the ion radius of a rare-earth metal.

$R^2$ affects the coordination ability, direction, and flexibility of the carboxyl group, and is independently selected from the group consisting of hydrogen atom, an aryl group, and an alkyl group, hydrogen atom being the most favorable.

$R^3$ represents a functional group expressed by $-R^{3-1}-R^{3-2}$, the definitions of which were given already and omitted.

When the hydrogen atom is selected as $R^3$ ($R^{3-1}$: none; $R^{3-2}$: hydrogen atom), in case of forming the complex of the fluorescent compound constituting the 1st aspect of this invention and a rare-earth metal ion, the rare-earth metal ion undergoes not only the coordination by planarly-disposed nitrogen atoms, but also by the carboxyl group from the axial direction, so that the stability of the complex thus obtained is improved.

Bulky functional group may also be selected as $R^3$, wherein it is possible to apply the fluorescent compound constituting the 1st aspect of this invention to the following measurement method for example.

Namely, because of the presence of bulky $R^3$, the fluorescent compound of this invention suffers a large axial steric hindrance, so that it can not form complex with a rare-earth metal ion. The measurement method then consists, for example, of transforming the fluorescent compound of this invention into the structure capable of coordinating the rare-earth metal ion by restoring the carboxyl group by removing $R^3$ specifically according to the amount of the target substance to be measured, of forming complex, and of measuring the fluorescence derived from complex.

In case of applying the fluorescent compound constituting the 1st aspect of this invention to such method, an aryl group, particularly a functional group expressed by the following formula E or F, is favorably selected as $R^3$.

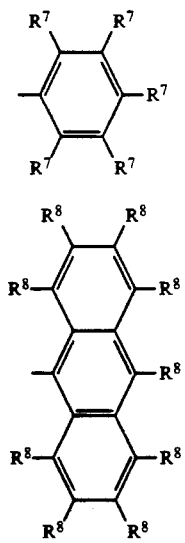

Formula E

Formula F $R^7$ in formula E is independently selected from the group consisting of hydrogen atom, an alkyl group, an alkenyl group, an alkynyl group, an aryl group, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group expressed by $-R^{7-1}-R^{7-2}$, wherein $-R^{7-1}-R^{7-2}$ is defined in the same manner as for $-R^{4-1}-R^{4-2}$ in formula A. The definition of $R^8$ in formula F is the same as that of $R^7$.

$R^4$ is independently selected from the group consisting of hydrogen atom, an alkyl group, an alkenyl group, an alkynyl group, an aryl group, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group expressed by $-R^{4-1}-R^{4-2}$ wherein the definition of $R^{4-1}$ and $R^{4-2}$ are described above and omitted, or it takes the form of either at least one aromatic ring or at least one heterocyclic ring including two or three carbon atoms which are the part of a phenanthroline ring as a result of ring-forming condensation brought about by the bonding of neighboring $R^4$ to each other.

The aromatic or heterocyclic ring is made up by the direct conjugative ring forming condensation of the two phenanthroline rings included in the basic skeleton of the fluorescent compound constituting the 1st aspect of this invention. As examples of such phenanthroline portion of the fluorescent compound bearing such $R^4$ constituting the 1st aspect of this invention the following formula G and H can be cited.

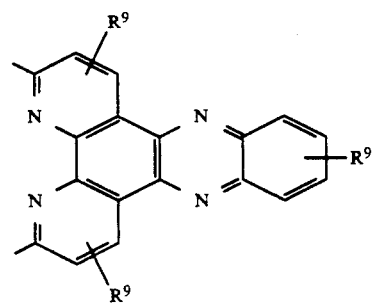

Formula G

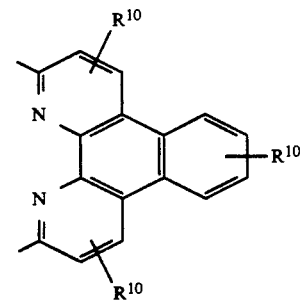

Formula H $R^9$ in formula G is independently selected from the group consisting of hydrogen atom, an alkyl group, an alkenyl group, an alkynyl group, an aryl group, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group expressed by $-R^{9-1}-R^{9-2}$ wherein $-R^{9-1}-R^{9-2}$ are defined in the same manner as for $-R^{4-1}-R^{4-2}$ in formula A. $R^{10}$ in formula H is defined in the same manner as for $R^9$.

The site of $R^4$ in the structure of the fluorescent compound constituting the 1st aspect of this invention hardly participates in the complex formation with a rare-earth metal ion, so that, as described precedingly, various functional groups can be introduced. Selecting appropriate functional group as $R^4$, it is possible to shift the optimum excitation wavelength of the complex formed from the fluorescent compound and the rare-earth metal ion to a favorable wavelength.

Generally, the higher energy efficiencies are obtained when the more conjugation systems are involved in the structural formula and, as the result, the fluorescence intensity of complex is enhanced.

Accordingly, it is particularly desirable to select an aryl group as $R^4$ for improving the absorption efficiency of the excitation light by selecting an optimum excitation wavelength, and for increasing the fluorescence intensity emitted from complex.

It is also desirable to select, as $R^4$, a functional group capable of bonding the fluorescent compound constituting the 1st aspect of this invention with the specific binding agent described later.

As an example of such functional group, the functional group expressed by $—R^{4-1}—R^{4-2}$, the definitions of which were described precedingly and omitted, can be cited but the concrete selection of functional group are affected by the structure of the portion participating in bond of the substance, to which the fluorescent compound of this invention is bound.

When, as an example, protein, a kind of specific binding agent, is selected to bond the fluorescent compound of this invention and the bonding portion is the amino group of the protein, $R^4$ is expressed by $—R^{4-1}—R^{4-2}$, and $R^{4-2}$ is selected from a group consisting of $—SO_2Cl$, $—N=C=S$, $—COOH$ and its derivative, maleimide group, and the like.

The value of m in preceding formula A is, each independently, 0 or 1 and, although the values of m in the four sites may well be either the same or different each other, it is desirable that the values of m in the four sites are the same, since it is preferred that the distance between the nitrogen atom participating in the complex formation and the rare-earth metal ion coordinated is the same to each other. The value of m is fixed to 0 or 1, since the value of m exceeding 2 causes the cavity size not fitting the radius of the rare-earth metal ion.

The value of n in preceding formula A is independently selected from integer ranging from 0 to 4. The value of n exceeding the integer 5 can bring about steric hindrance and, in case n is an integer exceeding 5 and $R^3$ is hydrogen atom, the coordination ability of carboxyl group to a rare-earth metal ion is lowered, so that the value of n is kept within the integer ranging 0 to 4.

As the fluorescent compound constituting the 1st aspect of this invention expressed by preceding formula A, compound expressed by the following formula B or C, particularly the compound with the basic skeleton expressed by the following formula I, is favored among others.

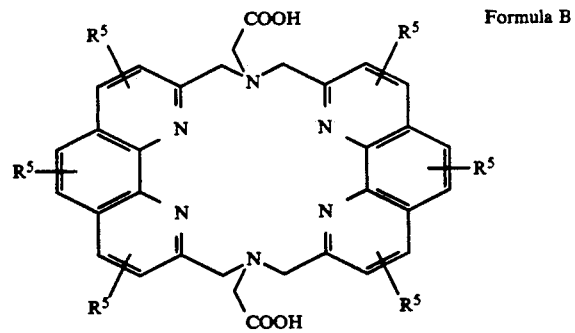

Formula B

Wherein $R^5$ is independently selected from the group consisting of hydrogen atom, an alkyl group, an alkenyl group, an alkynyl group, an aryl group, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group expressed by $—R^{5-1}—R^{5-2}$ defined in the same manner as for $—R^{4-1}—R^{4-2}$ in formula A.

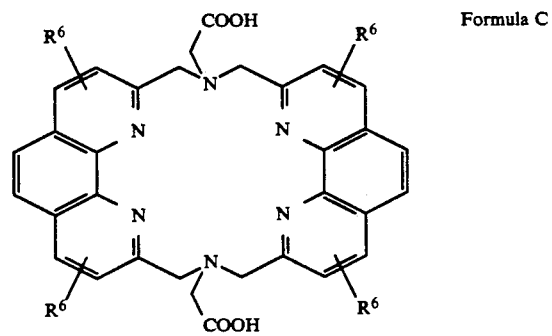

Formula C $R^6$ in formula C is independently selected from the functional groups expressed by formula D, wherein $—R^{6-1}—R^{6-2}$ is defined in the same manner as for $—R^{4-1}—R^{4-2}$ in formula A and k is an integer ranging from 0 to 5.

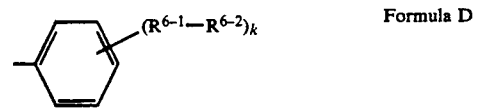

Formula D

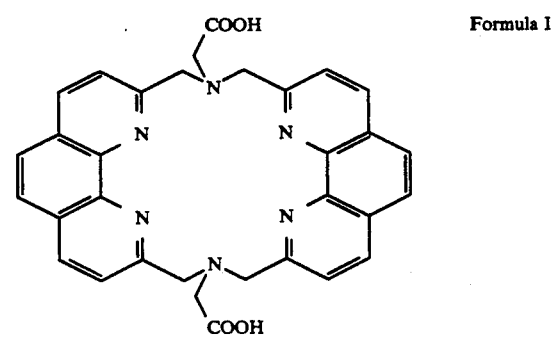

Formula I

As an example of the suitable synthetic procedures of the fluorescent compound constituting the 1st aspect of this invention, the synthetic procedure of the compound expressed preceding formula I is described below in accordance with FIG. 1.

As the 1st process, tosylation of compound (a) is carried out, followed by reacting compound (b), the tosylation product of compound (a), with compound (c).

The reason that compound (b) is reacted here with compound (c) is that the reaction of compound (a) with compound (c) produces the compound expressed by the following formula J which is not the desired compound.

Formula J

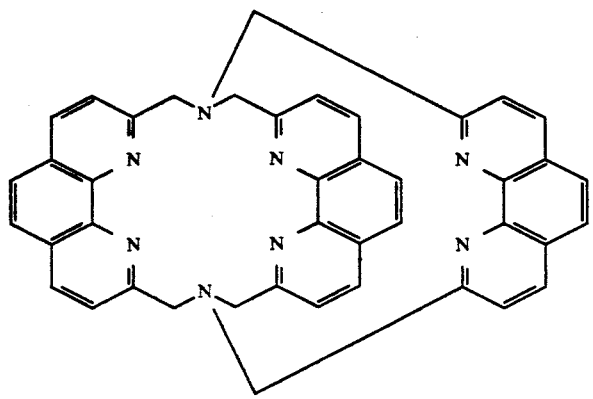

As the solvent to be employed in the reaction of compound (b) with compound (c), dimethylformamide, chloroform, tetrahydrofuran, and the like can be cited, dimethylformamide being favorable from the viewpoints of both the solubilities of compound (b) and compound (c) and the reaction yield. As the base to be employed in this reaction, potassium carbonate, sodium hydride, bis(dimethylamino)naphthalene, and the like are exemplified, potassium carbonate being favorable. Considering the yield, the reaction temperature of said reaction is preferred to range from 100° to 200° C. Purging of the whole reaction vessel with inert gas such as nitrogen or argon in order to prevent the deteriorations with oxygen of raw materials (compound (b) and/or compound (c)) and product (compound (d)) caused by the use of the high reaction temperature may be also recommended.

Detosylation of the compound (d) obtained is next carried out. Said detosylation reaction may be effected according to the well-known procedure described in the method by Bottino F. and others (J. Org. Chem., 53, 3521 (1988)) and others. A mixed solvent composed of sulfuric acid and acetic acid is preferable as the solvent for the detosylation. The reaction is preferred to be carried out at a temperature ranging from 60° to 100° C. for 12 hours or more, particularly at ca. 80° C. for ca. 12 hours. The use of reaction temperature 50° C. or below and/or short reaction time cause incomplete detosylation and leaves the starting material behind.

The ethoxycarbonylmethyl group is then introduced to the nitrogen atoms at the 2 and 15 positions of the detosylated compound (e), wherein, as the raw material for offering the ethoxycarbonylmethyl group, ethyl chloroacetate, ethyl bromoacetate, and the like can be cited; and, as base to be used as catalyst, potassium carbonate, bis(dimethylamino)naphthalene, diisopropylethyl amine, triethyl amine and others can be cited. The selections of ethyl bromoacetate as the raw material and potassium carbonate as the base are favorable. As the solvent to be used for the reaction system, dimethylformamide, chloroform, tetrahydrofuran, acetonitrile, and the like can be cited, particularly dimethylformamide being the solvent of choice.

Compound thus synthesized is compound (f), which is the fluorescent compound constituting the 1st aspect of this invention. It may be subjected to further deethylation to afford compound (g).

Deethylation may be carried out by the conventional method consisting of the hydrolysis with the hydroxide of alkali metal or alkali-earth metal using alcohol as solvent. Any alcohols may be selected as the solvent. Considering the solubility of compound (e), however, a lower saturated alcohol, particularly methanol or ethanol, is favorably selected. Any hydroxides not preventing the progress of said reaction may be employed, potassium hydroxide readily soluble in methanol or ethanol being preferable. The reaction is preferred to be carried out with refluxing for one hour or more in order to assure the hydrolysis.

The 2nd aspect of this invention is the complex composed of the fluorescent compound constituting the 1st aspect of this invention and a rare-earth metal ion.

As the rare-earth metal, europium, terbium, samarium, gadolinium, ytterbium, and others can be cited. From the viewpoint of fluorescence intensity, however, europium and terbium are particularly favorable and, including the viewpoint of fluorescence lifetime, europium is the compound of choice.

The complex constituting the 2nd aspect of this invention is characterized by that the unshared electron pair of the nitrogen atom situated at the center site of the ring structure of the fluorescent compound constituting the 1st aspect of this invention coordinates rare-earth metal ion.

When the fluorescent compound constituting the 1st aspect of this invention has the structure, wherein the functional group extending out of the nitrogen atom at the 2 and 15 positions possesses the carboxyl group at its end or said carboxyl group is restored under certain conditions, preceding rare-earth metal ion is also coordinated by said carboxyl group. Said coordination effected from the direction tilted ca.90 degree against the coordination by the unshared electron pair of the preceding nitrogen atom, so that the rare-earth metal ion becomes coordinated three-dimensionally to bring about the improved stability of the complex.

The complex constituting the 2nd aspect of this invention becomes very stable, since it possesses the preceding coordination characteristics and the cavity size of the fluorescent compound constituting the 1st aspect of this invention almost fits the ion radius of a rare-earth metal.

The complex constituting the 2nd aspect of this invention can be obtained by such methods as mixing the fluorescent compound constituting the 1st aspect of this invention with the salt of rare-earth metal.

The complex constituting the 2nd aspect of this invention emits characteristic fluorescence; the lifetime of fluorescence emitted from the complex of this invention is satisfactorily long, as compared with the lifetimes of fluorescence derived from other substances causing the background. Such being the case, the use of the complex of this invention permits measurement of the fluorescence derived from the complex of this invention after the background fluorescences have disappeared. Accordingly, the fluorescence emitted from the complex constituting the 2nd aspect of this invention is favorably measured by means of a time-resolved fluorophotometer, i.e. a fluorophotometer wherein the pulse excitation form is adopted and the time delay to remove the background fluorescence during the excitation and fluorescence detection by the gate function is provided. Another feature of the complex of this invention is showed by the fluorescence with large Stokes shift.

The 3rd aspect of this invention is constituted by the reagent composed of a specific binding agent and the fluorescent compound constituting the 1st aspect of this invention or the complex constituting the 2nd aspect of this invention, bonded directly or indirectly to the specific binding agent.

The specific binding agent composing the reagent constituting the 3rd aspect of this invention means the substance binding specifically to a certain substance. More concretely, antibody, antigen, hapten, hormone, protein, polypeptide, nucleic acid, polynucleotide, oligonucleotide, oligosaccharide, polysaccharide, and the like can be cited.

The bond formation between said specific binding agent and the fluorescent compound constituting the 1st aspect of this invention or the complex constituting the 2nd aspect of this invention may be carried out either directly or indirectly. In case direct bond is to be formed, the compound bearing the functional group which is selected in accordance with the structure of the portion participating in the bond by the specific binding agent is selected as the compound constituing the 1st aspect of this invention. As for the complex constituting the 2nd aspect of this invention, similar compound is also selected as the fluorescent compound constituting said complex.

Concretely, as the structure of the portion participating in the bond by the specific binding agent, reactive functional groups such as an amino group, carboxyl group, mercapto group, and aldehyde group can be cited; as functional groups on the side of the fluorescent compound reacting with these functional groups, succinimide ester group, isothiocyanate group, sulfonyl chloride group, an alkyl halide group, maleimide group, hydrazide group, and the like can be cited.

In order to bond the fluorescent compound having functional group described precedingly with the specific binding agent, the well-known method described in "Eiji Ishikawa, Method of Enzyme Immunoassay, 3rd Ed., Igaku Shoin, 75–151 (1987)" and others may be applied.

In order to isolate the labelled product out of the reaction mixture of the specific binding agent and the fluorescent compound or complex, purification procedures such as gel-filtration may be applied according to the well-known technics as described in the book or others.

In order to make bonding indirectly, on the other hand, proteins such as bovine serum albumin (BSA), thyroglobulin, avidin, and streptavidin, polypeptides such as poly-L-lysine, biotin, and/or the substance well-known as cross-linking agent may intervene between the fluorescent compound constituting the 1st aspect of this invention or the complex constituting the 2nd aspect of this invention and the specific binding agent.

The intervention of substance as described precedingly between the fluorescent compound constituting the 1st aspect of this invention or the complex constituting the 2nd aspect of this invention and the specific binding agent allows the preceding substance to bond a number of labelling agents (fluorescent compound or complex), so that the reagent bonded with a number of labelling agents can be obtained.

The substance intervening between the fluorescent compound constituting the 1st aspect of this invention or the complex constituting the 2nd aspect of this invention and the specific binding agent is not limited to one kind.

As an instance, by bonding avidin with fluorescent compound on the one hand and by bonding specific binding agent with biotin on the other, followed by binding avidin with biotin, the reagent wherein avidin and biotin intervene between the fluorescent compound and the specific binding agent can be obtained. The reagent can also be used, that the binding the avidin labelled with fluorescent compound with the specific binding agent labelled with biotin is performed during the reaction in the specific binding assay, described later.

Alternatively, by bonding fluorescent compound with BSA using the cross-linking agent on the other, by bonding specific binding agent with BSA using the cross-linking agent, the reagent wherein the cross-linking agent and BSA intervene between fluorescent compound and specific binding agent can be obtained.

As the general procedure for labelling either directly or indirectly the fluorescent compound or complex, the methods so far employed for bonding enzyme as the labelling agent with antibody and others in order to prepare the labelled reagent to be used for the enzyme immunoassay (EIA), such as glutaraldehyde method, periodate method, maleimide method, pyridyl disulfide method, and mixed acid anhydride method, or, if necessary, methods made up appropriately by improving these methods are exemplified.

In case the substance to be labelled is nucleic acid, use of the labelling method described in "DNA Probe II", written by Toyozo Takahashi and published by CMC Co. is preferred.

The reagent constituting the 3rd aspect of this invention can be used, in the measurement of a target substance existing in body fluids such as blood and urine and in industrial water, as a labelled specific binding agent. It is particularly useful in the measurement of a target substance in liquid sample.

A target substance in this invention means the substance to be measured. Concretely, it includes various substances existing in body fluids such as blood and urine, in industrial water and others, and, more concretely, drug, metabolite, physiologically active substance, chemical substance, natural substance, antibiotics, genetic substance, and others.

The reagent constituting the 3rd aspect of this invention can be prepared corresponding to any target substance. As the target substance appropriate for the measurement with these reagents, antibody, antigen, nucleic acid, polynucleotide, cell, hormone, virus, bacteria, protozoa, hapten, polypeptide, allergen, oligosaccharide, polysaccharide, and others can be cited.

As for the preparation of the reagent constituting the 3rd aspect of this invention, measuring method, not to speak of the kind of the corresponding target substance, must be considered.

In case the target substance is antigen, as a specific binding agent constituting a reagent of this invention, antibody, said antigen, or its analog is selected.

Similarly, in case the target substance is receptor, acceptor, said receptor, or its analog is selected as a specific binding agent.

In case the target substance is nucleic acid, the complementary nucleic acid, the same nucleic acid as the target substance, or its modified product is selected as a specific binding agent.

The 4th and 5th aspects of this invention are the specific binding assays of consisting in the measurement of a target substance in liquid sample, using the reagent constituting the 3rd aspect of this invention as labelled agent.

Wherein the liquid sample is intended to mean various kinds of body fluid such as blood, serum, plasma, urine, spinal fluid, and semen, liquids extracted from feces or tissue, industrial water, etc..

A specific binding assay means the immunoassay using the antigen-antibody reaction, assay using the receptor-acceptor binding reaction, assay using the hybridization of nucleic acid, etc..

A target substance means the substance to be measured and, concretely, the following substances are exemplified.

In case the specific binding assay is the immunoassay using the antigen-antibody reaction, substances as tumor marker such as alpha-fetoprotein (AFP), carcinoembryonic antigen (CEA), CA19-9, CA125, CA54/61, and CA602, substances capable of indicating the biological function such as ferritin and $\beta_2$-microglobulin ($\beta_2$-m), glyco-protein hormones and peptide hormones such as human chorionic gonadotropin (hCG), thyroid-stimulating hormone (TSH), follicle-stimulating hormone (FSH), and luteinizing hormone (LH), steroid hormones such as estrogen, progesterone, testosterone, and cortisol, virus antigen such as HBs-antigen, and antibody against it, namely, hapten, complete antigen and the antibody against them, are exemplified as a target substance.

As for the specific binding assay using the receptor-acceptor binding reaction, substances constituting the receptor-acceptor relationship such as androgen and androgen-receptor, estrogen and estrogen-receptor, insulin and insulin-receptor, thyroxine and thyroxine-receptor, glucocorticoid and glucocorticoid-receptor, can be cited as the target substance.

As for the specific binding assay using the hybridization of nucleic acid, nucleic acids such as DNA and RNA of viruses including hepatitis B virus (HBv) and hepatitis C virus (HCv) and DNA and RNA including chlamydiae, campylobacter, tubercle bacillus, multi-drug-resistant staphylococcus, and enterotoxigenic E. coli are exemplified as the target substance.

The specific binding assay constituting the 4th and 5th aspects of this invention can be practised by means of the sandwich method, the competitive method, and methods based on other principles.

In order to carry out the immunoassay for antigen (said target substance) in liquid sample using the sandwich method, a procedure as described below is adopted.

Such sandwich method requires two kinds of antibody, the 1st of which is employed as an immobilized antibody and the 2nd of which is used as a labelled antibody (reagent constituting the 3rd aspect of this invention). And, by measuring fluorescence activity in the immunological complex composed of two kinds of antibody and antigen, the amount of antigen can be determined.

More concretely, in the 4th aspect of this invention, the immune complex is obtained, for example, by incubating the antigen in liquid sample with the antibody labelled with fluorescent compound either directly or indirectly and the immobilized antibody. Said reaction may be carried out according to a method selected from the one-step and two-step procedures. Rare-earth metal ion was then added to form a complex of said fluorescent compound in labelled antibody and the rare-earth metal ion, followed by exciting said complex with irradiation by the excitation light of the appropriate wavelength and, if possible, after the background fluorescences derived from coexisting substances have disappeared, measuring the fluorescence intensity derived from said complex (time-resolved fluorescent assay).

In preceding method, addition of the rare-earth metal ion is not limited to after the formation of the immune complex. The formation of the complex of the fluorescent compound in labelled antibody and rare-earth metal ion prior to the reaction of the labelled antibody or the addition of the rare-earth metal ion during the reaction of the labelled antibody to form the complex may be allowed.

In the 5th aspect of this invention, as the labelled antibody wherein the complex composed of fluorescent compound and rare-earth metal ion is bonded either directly or indirectly to antibody is used, said labelled antibody and immobilized antibody are subjected to the reaction with antigen in liquid sample to form the immune complex, followed by exciting preceding complex with irradiation by the excitation light of the appropriate wavelength and, if possible, after the background fluorescences derived from coexisting substances have disappeared, measuring the fluorescence intensity derived from said complex.

In such sandwich method, fluorescence intensity is nearly in proportion to the amount of antigen. In order to enhance the fluorescence intensity, coexistence of surfactant agent and others is also allowed.

The measurement of antigen (said target substance) in liquid sample by means of the competitive method is carried out as follows.

As for the competitive method, two methods consisting of the use of labelled antigen or its analog and the use of labelled antibody as a labelled agent are presented. In this former method, antibody against antigen is immobilized and said immobilized antibody is subjected to the competition reaction with antigen in liquid sample and the labelled antigen or its analog constituting the 3rd aspect of this invention, followed by measuring the fluorescence intensity of the labelled antigen or its analog bound to immobilized antibody to determine the amount of antigen.

In the latter method, the labelled antibody, i.e. reagent constituting the 3rd aspect of this invention, is first bound to antigen in liquid sample, followed by reacting the labelled antibody not bound to antigen in liquid sample with the preliminarily immobilized antigen or its analog to determine the amount of antigen by measuring the fluorescence activity derived from the labelled antibody bound to the immobilized antigen or its analog.

In the competition method as in preceding sandwich one, the specific binding assay constituting the 4th aspect of this invention includes the operation that rare-earth metal ion is added in any stage prior to fluorescence measurement to form complex of the fluorescent compound in labelled antigen or labelled antibody and rare-earth metal ion, whereas, in the case of the specific binding assay constituting the 5th aspect of this invention, the addition of the rare-earth metal ion is not needed since labelled antigen or labelled antibody has been labelled with complex.

In the case of the competition method, the fluorescence intensity is almost inversely proportional to the amount of antigen.

The immunoassay, one of the specific binding assays constituting the 4th and 5th aspects of this invention, also permits the measurement of the antibody included in liquid sample, wherein the method using labelled antigen recognized by the antibody (reagent constituting the 3rd aspect of this invention) and that using the labelled antibody recognizing said antibody, i.e. labelled antibody as the 2nd antibody (reagent constituting the 3rd aspect of this invention), can be cited.

In the former method, the target antibody produced in the living body must be di- or multi-valent. And the fluorescence intensity derived from complex in the composite substance made up by binding said antibody to said two antigens as immobilized antigen and labelled antigen is measured.

The latter method consists of measuring the fluorescence intensity derived from complex in the composite substance made up by reacting the immobilized antigen first with the target antibody, and then with the 2nd antibody labelled with fluorescence compound, wherein the antigen may be also allowed to be immobilized by antibody against the antigen.

In the methods, the specific binding assay constituting the 4th aspect of this invention also requires the process of the addition of a rare-earth metal ion.

The specific binding assays constituting the 4th and 5th aspects of this invention allow the highly sensitive assays using the receptor and acceptor, wherein the well-known method described in "Development and Evaluation of New Biodiagnostic Reagent", Technical research report No. 1, CMC, pp. 48–57, can be employed, except that the reagent constituting the 3rd aspect of this invention is used as labelled agent and, in the specific binding assay constituting the 4th aspect of this invention, the process of adding a rare-earth metal ion is included.

Furthermore, the specific binding assays constituting the 4th and 5th aspects of this invention allow the assay based on the hybridization of nucleic acid.

As for the measurement of nucleic acid as the target substance in liquid sample, the nucleic acid complementary to the target substance is first prepared and then the reagent constituting the 3rd aspect of this invention is prepared using said complementary nucleic acid. For example, the assay is carried out as follows.

In the 1st method, nucleic acid extracted from biological sample is fixed to the solid phase, and the labelled probe (reagent constituting the 3rd aspect of this invention) is added to react with it. The presence or absence of nucleic acid as the target substance can be examined by measuring the fluorescence derived from the labelled probe remaining in the solid phase after the bound/free (B/F) separation. When the amount of the target nucleic acid in the sample is trace, the use well-known amplifying procedures of such as PCR method is allowed.

As the 2nd method, two kinds of the nucleic acid complementary to a portion of the sequence of the target nucleic acid have been prepared. The 1st nucleic acid has been fixed to the solidphase, then the target substance in biological sample is added and incubated, followed by reacting the labelled 2nd nucleic acid (reagent constituting the 3rd aspect of this invention) to make sandwich complex. After washing, fluorescence derived from said complex is measured, and the target substance is quantified by the fluorescence intensity.

In these methods, the specific binding assays constituting the 4th aspect of this invention also require the process of the addition of a rare-earth metal ion prior to the process of the fluorescence measurement.

Thus, in the 4th aspect of this invention, the reagent constituting the 3rd aspect of this invention composed of the fluorescent compound constituting the 1st aspect of this invention and the specific binding agent bonded directly or indirectly is used, and the specific binding assays comprising the process of complexation with said fluorescent compound and a rare-earth metal ion, and the process of the fluorescence measurement of said complex, such as immunoassay, assay using the receptor-acceptor binding reaction, assay using the hybridization of nucleic acid, etc. are included.

In the 5th aspect of this invention, the reagent constituting the 3rd aspect of this invention composed of the complex constituting the 2nd aspect of this invention and the specific binding agent bonded directly or indirectly is used, and the specific binding assays comprising the process of the fluorescence measurement of said complex, such as immunoassay, assay using the receptor-acceptor binding reaction, assay using the hybridization of nucleic acid, etc. are included.

The invention is further illustrated by the following nonlimiting examples.

EXAMPLE 1

Synthesis of 2,15-diaza[3.3](2,9)-1,10-phenanthrolinophane-$N^2,N^{15}$-diacetic acid 2,15-Diaza[3.3](2,9)-1,10-phenanthrolinophane-$N^2,N^{15}$-diacetic acid was synthesized as shown in FIG. 1, and these reactions were carried out as follows.

(1) Synthesis of 2,9-bis(aminomethyl)-1,10-phenanthroline perchlorate (a)

2,9-Bis(aminomethyl)-1,10-phenanthroline perchlorate was synthesized from 2,9-dimethyl-1,10-phenanthroline according to the method described in J. Heterocyclic Chem., 18, 599 (1981).

(2) Synthesis of 2,9-bis(tosylaminomethyl)-1,10-phenanthroline (b)

2,9-Bis(aminomethyl)-1,10-phenanthroline perchlorate (a) (1.76 g, 4 mmol) synthesized in Example 1(1)

was dissolved in pyridine (20 ml). p-Toluenesulfonyl chloride (1.6 g, 8 mmol) was added to the solution with cooling using an ice bath, then the reaction mixture was stirred at room temperature for 3 hours. The resulting solution was poured into water (200 ml) and extracted with chloroform (200 ml). The chloroform layer was chromatographed on a silica gel column using chloroform/methanol as eluent to give the desired 2,9-bis(tosylaminomethyl)-1,10-phenanthroline (b) (yield=1.87 g).

(3) Synthesis of 2,9-bis(bromomethyl)-1,10-phenanthroline (c)

2,9-Bis(bromomethyl)-1,10-phenanthroline was synthesized from 2,9-dimethyl-1,10-phenanthroline according to the method described in J. Heterocyclic Chem., 18, 599 (1981).

(4) Synthesis of $N^2,N^{15}$-ditosyl-2,15-diaza[3.3](2,9)-1,10-phenanthrolinophane (d)

2,9-Bis(tosylaminomethyl)-1,10-phenanthroline (b) (628 mg, 1.15 mmol) synthesized in Example 1(2) and 2,9-bis(bromomethyl)-1,10-phenanthroline (c) (420 mg, 1.15 mmol) synthesized in Example 1(3) were dissolved in dimethylformamide (500 ml). Potassium carbonate (5 g) was added to the solution, and the mixture was heated at 120° C. for 4 hours with stirring. After being cooled, the reaction mixture was filtered, and the filtrate was evaporated. Water was added to the residue, and the resulting precipitate was collected to give the desired $N^2,N^{15}$-ditosyl-2,15-diaza[3.3](2,9)-1,10-phenanthrolinophane (d) (yield=310 mg).

(5) Synthesis of 2,15-diaza[3.3](2,9)-1,10-phenanthrolinophane (e)

$N^2,N^{15}$-Ditosyl-2,15-diaza[3.3](2,9)-1,10-phenanthrolinophane (d) (310 mg) synthesized in Example 1(4) was dissolved in a mixture of sulfuric acid (4 ml) and acetic acid (6 ml), and the solution was heated at 80° C. for 20 hours with stirring. The resulting solution was poured into ice water (100 ml) and neutralized with sodium hydroxide. The formed precipitate was filtered, and the filtrate was washed with water. Drying in reduced pressure the desired 2,15-diaza[3.3](2,9)-1,10-phenanthrolinophane (e) (yield=180 mg).

(6) Synthesis of 2,15-diaza[3.3](2,9)-1,10-phenanthrolinophane-$N^2,N^{15}$-diacetic acid diethyl ester (f)

2,15-Diaza[3.3](2,9)-1,10-phenanthrolinophane (e) (180 mg) synthesized in Example 1(5) was dissolved in dimethylformamide (100 ml), and then potassium carbonate (2 g) and ethyl bromoacetate (2 ml) were added. The mixture was heated at 100° C. for 12 hours with stirring. After being cooled, the reaction mixture was filtered, and the filtrate was evaporated. The residue was chromatographed on a silica gel column using chloroform/methanol as eluent to give the desired 2,15-diaza[3.3](2,9)-1,10-phenanthrolinophane-$N^2,N^{15}$-diacetic acid diethyl ester (f) (yield=40 mg).

(7) Synthesis of 2,15-diaza[3.3](2,9)-1,10-phenanthrolinophane-$N^2,N^{15}$-diacetic acid (g)

2,15-Diaza[3.3](2,9)-1,10-phenanthrolinophane-$N^2,N^{15}$-diacetic acid diethyl ester (f) (40 mg) synthesized in Example 1(6) was dissolved in methanol (10 ml), and potassium hydroxide (50 mg) was added. The mixture was heated at 50°–100° C. for 2 hours. The resulting solution was evaporated, and water (10 ml) was added. The solution was neutralized with diluted hydrochloric acid. The formed precipitate was collected to give the desired 2,15-diaza[3.3](2,9)-1,10-phenanthrolinophane-$N^2,N^{15}$-diacetic acid (g) (yield=30 mg).

EXAMPLE 2

Figure 2:
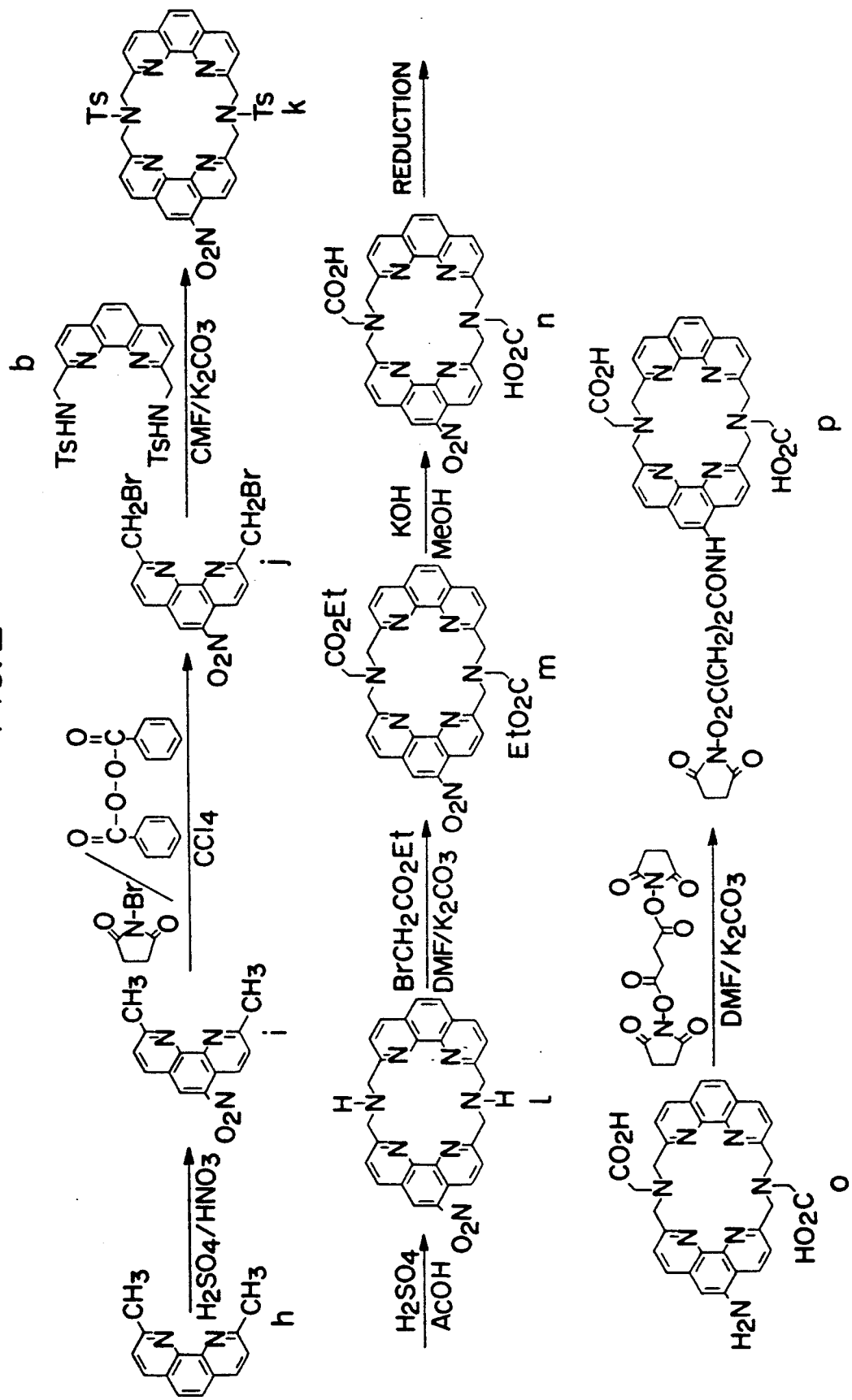
FIG. 2: The synthetic route of 8-(3'-succinimidyloxycarbonylpropionamide-2,15-diaza[3,3](2,9)-1,10-phenanthrolinophane-$N^2,N^{15}$-diacetic acid described in Example 2.

Synthesis of 8-(3'-succinimidyloxycarbonylpropionamide)-2,15-diaza[3.3](2,9)-1,10-phenanthrolinophane-$N^2,N^{15}$-diacetic acid 8-(3'-succinimidyloxycarbonylpropionamide)-2,15-diaza[3.3](2,9)-1,10-phenanthrolinophane-$N^2,N^{15}$-diacetic acid was synthesized as shown in FIG. 2, and these reactions were carried out as follows.

(1) Synthesis of 5-nitro-2,9-dimethyl-1,10-phenanthroline (i)

2,9-Dimethyl-1,10-phenanthroline (h) (20 g) was dissolved in a mixture of sulfuric acid (120 ml) and nitric acid (40 ml), and the mixture was heated at 100° C. for 12 hours with stirring. The resulting solution was poured into ice water (300 ml), and the formed precipitate was collected. The precipitate was dissolved in water (500 ml) and neutralized with sodium hydroxide. The resulting precipitate was collected and recrystallized from methanol (300 ml) to give the desired 5-nitro-2,9-dimethyl-1,10-phenanthroline (i) (yield=8.8 g).

(2) Synthesis of 5-nitro-2,9-bis(bromomethyl)-1,10-phenanthroline (j)

5-Nitro-2,9-dimethyl-1,10-phenanthroline (i) (8.4 g, 0.03 mol) synthesized in Example 2(1) was dissolved in carbon tetrachloride (500 ml), and then N-bromosuccinimide (10.7 g, 0.06 mol) and benzoyl peroxide (300 mg) were added. The mixture was refluxed at 80° C. for 12 hours. After evaporation of the resulting solution, 200 ml of benzene was added. The insoluble material was filtered off, and the filtrate was evaporated. The residue was purified by a silica gel column chromatography using benzene/ethyl acetate as eluent to give the desired 5-nitro-2,9-bis(bromomethyl)-1,10-phenanthroline (j) (yield=500 mg).

(3) Synthesis of 8-nitro-$N^2,N^{15}$-ditosyl-2,15-diaza[3.3](2,9)-1,10-phenanthrolinophane (k)

5-Nitro-2,9-bis(bromomethyl)-1,10-phenanthroline (j) (410 mg, 1 mmol) synthesized in Example 2(2) and 2,9-bis(tosylaminomethyl)-1,10-phenanthroline (b) (547 mg, 1 mmol) (see Example 1(2)) were dissolved in dimethylformamide (500 ml), and then potassium carbonate (5 g) was added. The mixture was heated at 120° C. for 4 hours with stirring. After being cooled, the resulting mixture was filtered, and the filtrate was evaporated. Water was added to the residue, and the resulting precipitates were collected and washed with water. Drying in reduced pressure the desired 8-nitro-$N^2,N^{15}$-ditosyl-2,15-diaza[3.3](2,9)-1,10-phenanthrolinophane (k) (yield=380 mg).

(4) Synthesis of 8-nitro-2,15-diaza[3.3](2,9)-1,10-phenanthrolinophane (l)

8-Nitro-$N^2,N^{15}$-ditosyl-2,15-diaza[3.3](2,9)-1,10-phenanthrolinophane (k) (380 mg) synthesized in Example 2(3) was dissolved in a mixture of sulfuric acid (4 ml) and acetic acid (6 ml). The reaction mixture was heated at 80° C. for 20 hours with stirring. The resulting solution was poured into ice water (100 ml) and neutralized with sodium hydroxide. The resulting precipitate was collected to give the desired 8-nitro-2,15-diaza[3.3](2,9)-1,10-phenanthrolinophane (l) (yield=230 mg).

(5) Synthesis of 8-nitro-2,15-diaza[3.3](2,9)-1,10-phenanthrolinophane-$N^2,N^{15}$-diacetic acid diethyl ester (m)

8-Nitro-2,15-diaza[3.3](2,9)-1,10-phenanthrolinophane (l) (230 mg) synthesized in Example 2(4) was dissolved in dimethylformamide (100 ml), and then potassium carbonate (2 g) and ethyl bromoacetate (2 ml) were added. The mixture was heated at 100° C. for 12 hours. The reaction mixture was filtered, and the filtrate was evaporated. The residue was chromatographed on a silica gel column using chloroform/methanol as eluent to give the desired 8-nitro-2,15-diaza[3.3](2,9)-1,10-phenanthrolinophane-$N^2,N^{15}$-diacetic acid diethyl ester (m) (yield=65 mg).

(6) Synthesis of 8-nitro-2,15-diaza[3.3](2,9)-1,10-phenanthrolinophane-$N^2,N^{15}$-diacetic acid (n)

8-Nitro-2,15-diaza[3.3](2,9)-1,10-phenanthrolinophane-$N^2,N^{15}$-diacetic acid diethyl ester (m) (65 mg) synthesized in Example 2(5) was dissolved in methanol (10 ml), and then potassium hydroxide (50 mg) was added. The mixture was refluxed at 80° C. for 2 hours. The resulting solution was evaporated, and water (10 ml) was added to the residue. The solution was neutralized with diluted hydrochloric acid. The formed precipitate was filtered to give the desired 8-nitro-2,15-diaza[3.3](2,9) 1,10-phenanthrolinophane-$N^2,N^{15}$-diacetic acid (n) (yield=40 mg)

(7) Synthesis of 8-amino-2,15-diaza[3.3](2,9)-1,10-phenanthrolinophane-$N^2,N^{15}$-diacetic acid (o)

8-Nitro 2,15-diaza[3.3](2,9)-1,10-phenanthrolinophane-$N^2,N^{15}$-diacetic acid (n) (40 mg) synthesized in Example 2(6) was dissolved in ethanol (15 ml), and 5% palladium on carbon (20 mg) was added. The suspension was stirred for 20 hours under hydrogen atmosphere. The resulting mixture was filtered, and then the filtrate was evaporated to give the desired 8-amino-2,15-diaza[3.3](2,9)-1,10-phenanthrolinophane-$N^2,N^{15}$-diacetic acid (o) (yield=25 mg) as an amorphous solid.

(8) Synthesis of 8-(3'-succinimidyloxycarbonylpropionamide)-2,15 diaza[3.3](2,9)-1,10-phenanthrolinophane-$N^2,N^{15}$-diacetic acid (p)

8-Amino-2,15-diaza[3.3](2,9)-1,10-phenanthrolinophane-$N^2,N^{15}$-diacetic acid (o) (25 mg) synthesized in Example 2(7) was dissolved in dimethylformamide (10 ml), and then disuccinimidylsuccinate (310 mg) and potassium carbonate (500 mg) were added. The mixture was heated at 80° C. for 15 hours with stirring. The reaction mixture was filtered, and the filtrate was evaporated. The residue was chromatographed on a silica gel column using chloroform/methanol as eluent to give the desired 8-(3'-succinimidyloxycarbonylpropionamide)-2,15-diaza[3.3](2,9)-1,10-phenanthrolinophane-$N^2,N^{15}$-diacetic acid (p) (yield=15 mg).

EXAMPLE 3

Figure 3:
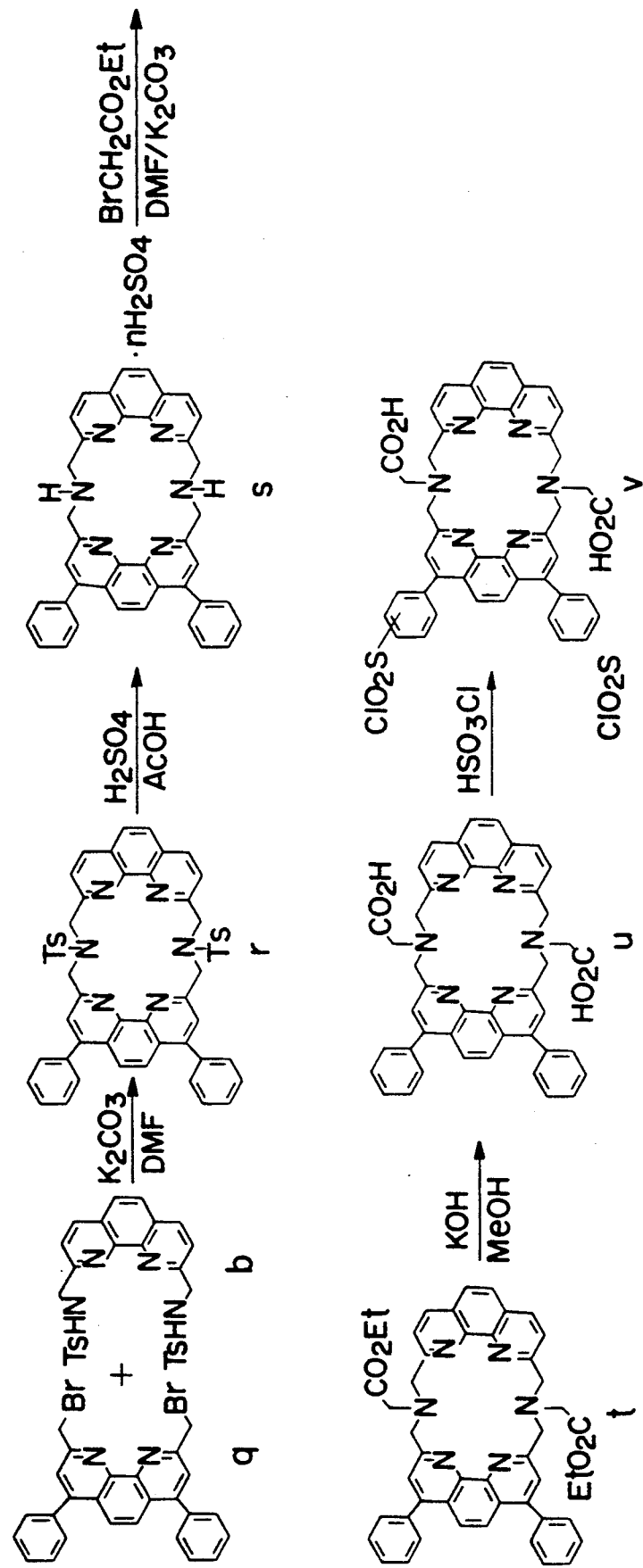
FIG. 3: The synthetic route of 7,10-diphenyl-2,15-diaza[3,3](2,9)-1,10-phenanthrolinophane-$N^2,N^{15}$-diacetic acid and 7,10-bis(chlorosulfophenyl)-2,15-diaza[3,3](2,9)-1,10-phenanthrolinophane-$N^2,N^{15}$-diacetic acid.

Synthesis of 7,10-diphenyl-2,15-diaza[3.3](2,9)-1,10-phenanthrolinophane-$N^2,N^{15}$-diacetic acid 7,10-Diphenyl-2,15-diaza[3.3](2,9)-1,10-phenanthrolinophane-$N^2,N^{15}$-diacetic acid was synthesized as shown in FIG. 3, and these reactions were carried out as follows.

(1) Synthesis of 2,9-bis(bromomethyl)-4,7-diphenyl-1,10-phenanthroline (q)

2,9-Bis(bromomethyl)-4,7-diphenyl-1,10-phenanthroline was synthesized from 2,9-dimethyl-4,7-diphenyl-1,10-phenanthroline according to the method described in J. Heterocyclic Chem., 18, 599 (1981).

(2) Synthesis of $N^2,N^{15}$-ditosyl-7,10-diphenyl-2,15-diaza[3.3](2,9)-1,10-phenanthrolinophane (r)

2,9-Bis(bromomethyl) 4,7-diphenyl-1,10-phenanthroline (q) (465 mg, 0.9 mmol) synthesized in Example 3(1) and 2,9-bis(tosylaminomethyl)-1,10-phenanthroline (b) (490 mg, 0.9 mmol) (see Example 1(2)) were dissolved in dimethylformamide (20 ml), and then potassium carbonate (2 g) was added. The mixture was heated at 120° C. for 4 hours with stirring. After being cooled, the reaction mixture was filtered, and the filtrate was evaporated. Water was added to the residue, and the resulting precipitate was filtered and recrystallized from chloroform to give the desired $N^2,N^{15}$-ditosyl-7,10-diphenyl-2,15-diaza[3.3](2,9)-1,10-phenanthrolino phane (r) (yield=740 mg).

(3) Synthesis of 7,10-diphenyl-2,15-diaza[3.3](2,9)-1,10-phenanthrolinophane sulfate (s)

$N^2,N^{15}$-ditosyl-7,10-diphenyl-2,15-diaza[3.3](2,9)-1,10-phenanthrolinophane (r) (720 mg) synthesized in Example 3(2) was dissolved in a mixture of sulfuric acid (6 ml) and acetic acid (9 ml). The reaction mixture was heated at 80° C. for 20 hours with stirring. The resulting solution was poured into ice water (100 ml). The resulting precipitate was filtered and washed with water. Drying in reduced pressure gave the desired 7,10-diphenyl-2,15-diaza[3.3](2,9)-1,10-phenanthrolinophane sulfate (s) (yield=430 mg).

(4) Synthesis of 7,10-diphenyl-2,15-diaza[3.3](2,9)-1,10-phenanthrolinophane-$N^2,N^{15}$-diacetic acid diethyl ester (t)

7,10-Diphenyl-2,15-diaza[3.3](2,9)-1,10-phenanthrolinophane sulfate (s) (380 mg) synthesized in Example 3(3) was dissolved in dimethylformamide (10 ml), and then potassium carbonate (2 g) and ethyl bromoacetate (2 ml) were added. The mixture was heated at 100° C. for 12 hours with stirring. The reaction mixture was filtered, and the filtrate was evaporated. The residue was chromatographed on a silica gel column using chloroform/methanol as eluent to give the desired 7,10-diphenyl-2,15-diaza[3.3](2,9)-1,10-phenanthrolinophane-$N^2,N^{15}$-diacetic acid diethyl ester (t) (yield=180 mg).

(5) Synthesis of 7,10-diphenyl-2,15-diaza[3.3](2,9)-1,10-phenanthrolinophane-$N^2,N^{15}$-diacetic acid (u)

7,10-Diphenyl-2,15-diaza[3.3](2,9)-1,10-phenanthrolinophane-$N^2,N^{15}$-diacetic acid diethyl ester (t) (40 mg) synthesized in Example 3(4) was dissolved in methanol (10 ml), and then potassium hydroxide (50 mg) was added. The mixture was refluxed at 80° C. for 2 hours. The resulting solution was evaporated, and water (10 ml) was added to the residue. The solution was neutralized with diluted hydrochloric acid. The formed precipitate was collected to give the desired 7,10-diphenyl-2,15-diaza[3.3](2,9)-1,10-phenanthrolinophane-$N^2,N^{15}$-diacetic acid (u) (yield=65 mg).

EXAMPLE 4

Synthesis of 7,10-bis(chlorosulfophenyl)-2,15-diaza[3.3](2,9)-1,10-phenanthrolinophane-$N^2,N^{15}$-diacetic acid 7,10-Bis(chlorosulfophenyl)-2,15-diaza[3.3](2,9)-1,10-phenanthrolinophane-$N^2,N^{15}$-diacetic acid was synthesized as shown in FIG. 3, and these reactions were carried out as follows.

7,10-Diphenyl-2,15-diaza[3.3](2,9)-1,10-phenanthrolinophane-$N^2,N^{15}$ diacetic acid (u) (60 mg) synthesized in Example 3 was dissolved in chlorosulfonic acid (1 ml), and the mixture was heated at 80° C. for 4 hours with stirring. The resulting solution was poured into ice water, and the formed precipitate was collected and washed with water. Drying in reduced pressure gave the desired 7,10-bis(chlorosulfophenyl)-2,15- diaza[3.3](2,9)-1,10-phenanthrolinophane-N$^2$,N$^{15}$-diacetic acid (v) (yield=45 mg).

EXAMPLE 5

Figure 4:
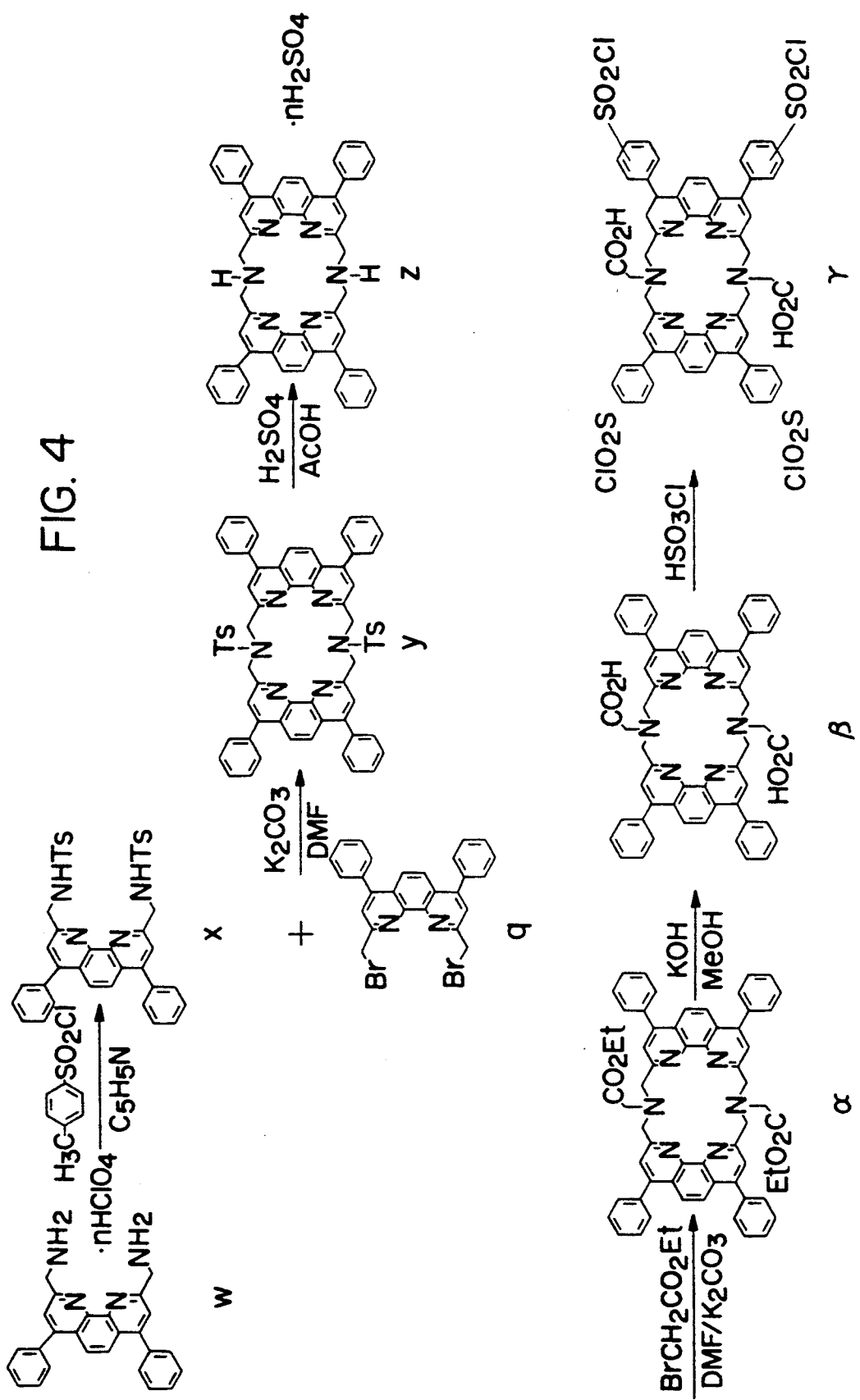
FIG. 4: The synthetic route of 7,10,20,23-tetrakis(-chlorosulfophenyl)-2,15-diaza[3,3](2,9)-1,10-phenanthrolinophane-$N^2,N^{15}$-diacetic acid described in Example 5.

Synthesis of 7,10,20,23-tetrakis(chlorosulfophenyl)-2,15-diaza[3.3](2,9)-1,10-phenanthrolinophane-N$^2$,N$^{15}$-diacetic acid 7,10,20,23-Tetrakis(chlorosulfophenyl)-2,15-diaza[3.3](2,9)-1,10-phenanthrolinophane-N$^2$,N$^{15}$-diacetic acid was synthesized as shown in FIG. 4, and these reactions were carried out as follows.

(1) Synthesis of 2,9-bis(tosylaminomethyl)-4,7-diphenyl-1,10-phenanthroline (x)

2,9-Bis(aminomethyl)-4,7-diphenyl-1,10-phenanthroline perchlorate (w) (2.36 g, 4 mmol), which was synthesized from 2,9-dimethyl-4,7-diphenyl-1,10-phenanthroline according to the method described in J. Heterocyclic Chem., 18, 599 (1981), was dissolved in pyridine (20 ml). p-Toluene sulfonyl chloride (1.6 g, 8 mmol) was added to the solution with cooling using an ice bath, and the reaction mixture was stirred at room temperature for 3 hours. The resulting solution was poured into water (200 ml) and extracted with chloroform (200 ml). The chloroform layer was chromatographed on a silica gel column using chloroform/methanol as eluent to give the desired 2,9-bis(tosylaminomethyl)-4,7-diphenyl-1,10-phenanthroline (x) (yield=1.54 g).

(2) Synthesis of N$^2$,N$^{15}$-ditosyl-7,10,20,23-tetraphenyl-2,15-diaza[3.3](2,9)-1,10-phenanthrolinophane (y)

2,9-Bis(bromomethyl)-4,7-diphenyl-1,10-phenanthroline (q) (520 mg, 1.0 mmol) (see Example 3(1)) and 2,9-bis(tosylaminomethyl)-4,7-diphenyl-1,10-phenanthroline (x) (700 mg, 1.0 mmol) synthesized in Example 5(1) were dissolved in dimethylformamide (20 ml), and then potassium carbonate (2 g) was added. The mixture was heated at 120° C. for 4 hours with stirring. After being cooled, the resulting solution was filtered, and the filtrate was evaporated. Water was added to the residue, and the resulting precipitate was filtered and recrystalized from chloroform to give the desired N$^2$,N$^{15}$-ditosyl-7,10,20,23-tetraphenyl-2,15-diaza[3.3](2,9)-1,10-phenanthrolinophane (y) (yield=790 mg).

(3) Synthesis of 7,10,20,23-tetraphenyl-2,15-diaza[3,3](2,9)-1,10-phenanthrolinophane sulfate (z)

N$^2$,N$^{15}$-Ditosyl-7,10,20,23-tetraphenyl-2,15-diaza[3.3](2,9)-1,10-phenanthrolinophane (y) (740 mg) synthesized in Example 5(2) was dissolved in a mixture of sulfuric acid (6 ml) and acetic acid (9 ml), and then the reaction mixture was heated at 80° C. for 20 hours with stirring. The resulting solution was poured into ice water (100 ml), and the formed precipitate was filtered and washed with water. Drying in reduced pressure gave the desired 7,10,20,23-tetraphenyl-2,15-diaza[3,3](2,9)-1,10-phenanthrolinophane sulfate (z) (yield=445 mg).

(4) Synthesis of 7,10,20,23-tetraphenyl-2,15-diaza[3.3](2,9)-1,10-phenanthrolinophane-N$^2$,N$^{15}$-diacetic acid diethyl ester ($\alpha$)

7,10,20,23-Tetraphenyl-2,15-diaza[3,3](2,9)-1,10-phenanthrolinophane sulfate (z) (410 mg) synthesized in Example 5(3) was dissolved in dimethylformamide (10 ml), and then potassium carbonate (2 g) and ethyl bromoacetate (2 ml) were added. The mixture was heated at 100° C. for 12 hours. The reaction mixture was filtered, and the filtrate was evaporated. The residue was chromatographed on a silica gel column using chloroform/methanol as eluent to give the desired 7,10,20,23-tetraphenyl-2,15-diaza[3.3](2,9)-1,10-phenanthrolinophane-N$^2$,N$^{15}$-diacetic acid diethyl ester ($\alpha$) (yield=190 mg).

(5) Synthesis of 7,10,20,23-tetraphenyl-2,15-diaza[3.3](2,9)-1,10-phenanthrolinophane-N$^2$,N$^{15}$-diacetic acid ($\beta$)

7,10,20,23-Tetraphenyl-2,15-diaza[3.3](2,9)-1,10-phenanthrolinophane-N$^2$,N$^{15}$-diacetic acid diethyl ester ($\alpha$) (185 mg) synthesized in Example 5(4) was dissolved in methanol (10 ml), and then potassium hydroxide (50 mg) was added. The mixture was refluxed for 2 hours. After being evaporated, the resulting solution was diluted with water (10 ml) and neutralized with diluted hydrochloric acid. The resulting precipitate was collected to give the desired 7,10,20,23-tetraphenyl-2,15-diaza[3.3](2,9)-1,10-phenanthrolinophane-N$^2$,N$^{15}$-diacetic acid ($\beta$) (yield=105 mg)

(6) Synthesis of 7,10,20,23-tetrakis(chlorosulfophenyl)-2,15-diaza[3.3](2,9) 1,10 phenanthrolinophane-N$^2$,N$^{15}$-diacetic acid ($\gamma$)

7,10,20,23-Tetraphenyl-2,15-diaza[3 3](2,9)-1,10-phenanthrolinophane-N$^2$,N$^{15}$-diacetic acid ($\beta$) (86 mg) synthesized in Example 5(5) was dissolved in chlorosulfonic acid (1 ml) and heated at 80° C. for 4 hours. The resulting solution is poured into ice water (20 ml), and then the resulting precipitate was filtered and washed with water. Drying in reduced pressure gave the desired 7,10,20,23-tetrakis(chlorosulfophenyl)-2,15-diaza[3.3](2,9)-1,10-phenanthrolinophane-N$^2$,N$^{15}$-diacetic acid ($\gamma$) (yield=60 mg)

EXAMPLE 6

Synthesis of 7,10-diphenyl-2,15-diaza[3.3](2,9)-1,10-phenanthrolinophane-N$^2$,N$^{15}$-diacetic acid, europium salt (PAPPA-Eu)

7,10-Diphenyl-2,15-diaza[3.3](2,9)-1,10-phenanthrolinophane-N$^2$,N$^{15}$-diacetic acid (u) (90 mg) synthesized in Example 3 was dissolved in 50% methanol/water (50 ml), and europium chloride (100 mg) was added. The mixture was refluxed for 1 hour. After evaporation of the resulting solution, the residue was dissolved in chloroform (50 ml) and washed with 5% potassium chloride solution (20 ml) to remove unreacted europium chloride. The chloroform layer was dried and evaporated. The residue was chromatographed on a silica gel column using chloroform/methanol as eluent to give the desired 7,10-diphenyl-2,15-diaza[3.3](2,9)-1,10-phenanthrolinophane-N$^2$,N$^{15}$-diacetic acid, europium salt (PAPPA-Eu) (yield=40 mg).

The structure of the synthetic compound was identified by mass spectrum analysis and elemental analysis.

EXAMPLE 7

Figure 5:
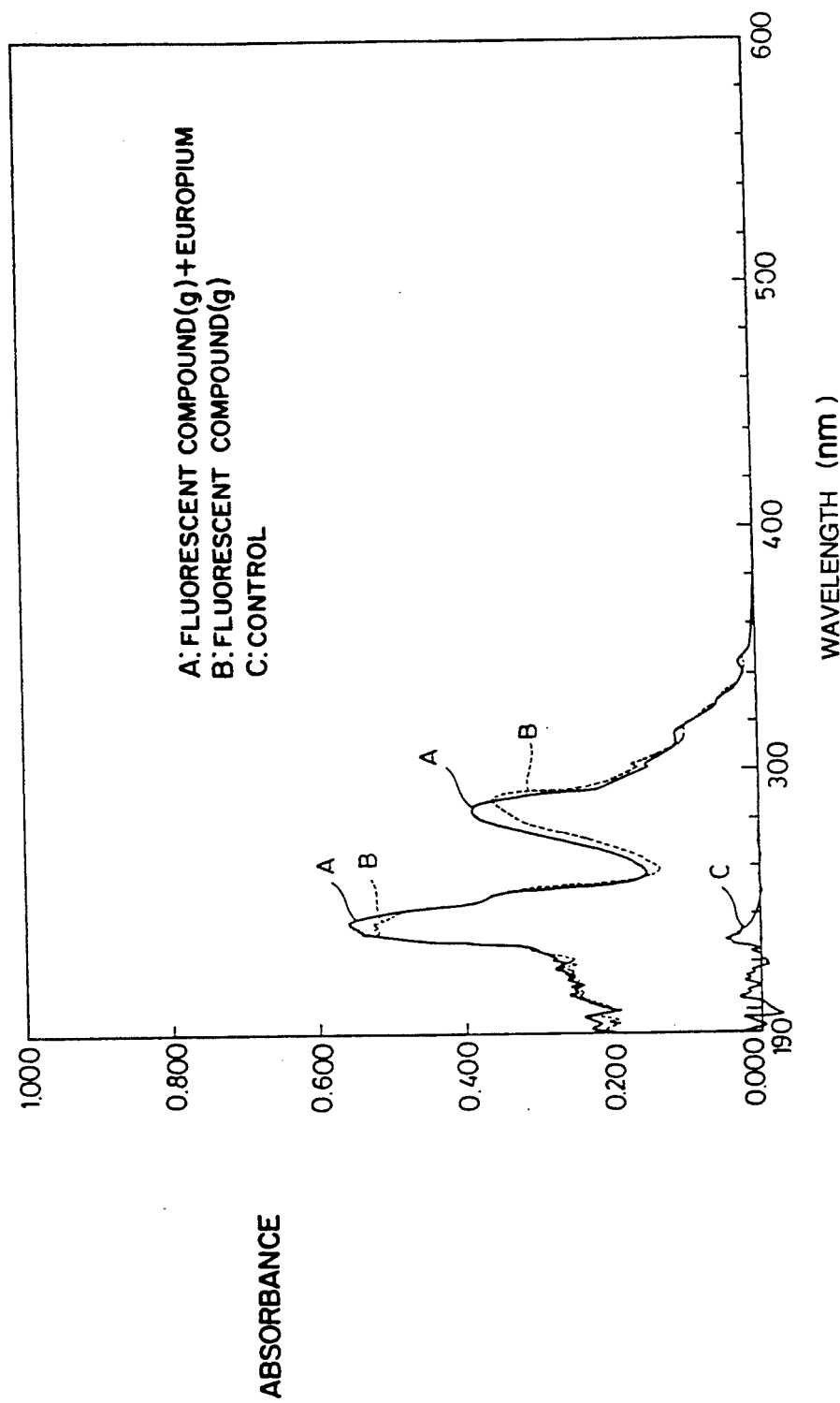
FIG. 5: The absorption spectrum for the complex formed from fluorescent compound (g) and europium ion described in Example 7.

Fluorescent characteristics of the europium complex of 2,15-diaza[3.3](2,9)-1,10-phenanthrolinophane N$^2$,N$^{15}$-diacetic acid (1) Measurement of absorption spectrum 2,15-Diaza[3.3](2,9)-1,10-phenanthrolinophane-N$^2$,N$^{15}$-diacetic acid (g) (fluorescent compound (g), 0.8 mg) synthesized in Example 1 was dissolved in 458 $\mu$l of dimethylsulfoxide and diluted in 5.3 ml of distilled water (fluorescent compound (g) solution). Europium chloride (788 mg) was dissolved in 21.5 ml of distilled water (europium chloride solution). Fluorescent compound (g) solution (80 $\mu$l) and europium chloride solution (80 μl) were mixed with 2 ml of 0.1 M sodium carbonate buffer (pH 10.5). Thirty minutes after the mixing, absorption spectrum was measured by a spectrophotometer (UV-2100, Shimadzu Corporation) (FIG. 5). Absorption spectra of a mixed solution of dimethylsulfoxide and distilled water in 0.1 M sodium carbonate buffer (pH 10.5) and a solution excluding europium chloride from the sample solution were also measured as controls (FIG. 5).

(2) Measurement of excitation and emission spectra

Fluorescent compound (g) solution (30 μl) and europium chloride solution (30 μl) were mixed with 3 ml of 0.1 M sodium carbonate buffer (pH 10.5). Thirty minutes after the mixing, excitation and emission spectra of the mixed solution were measured by JASCO FP-777 spectrofluorometer (Japan Spectroscopic Co., Ltd.).

Figure 6:
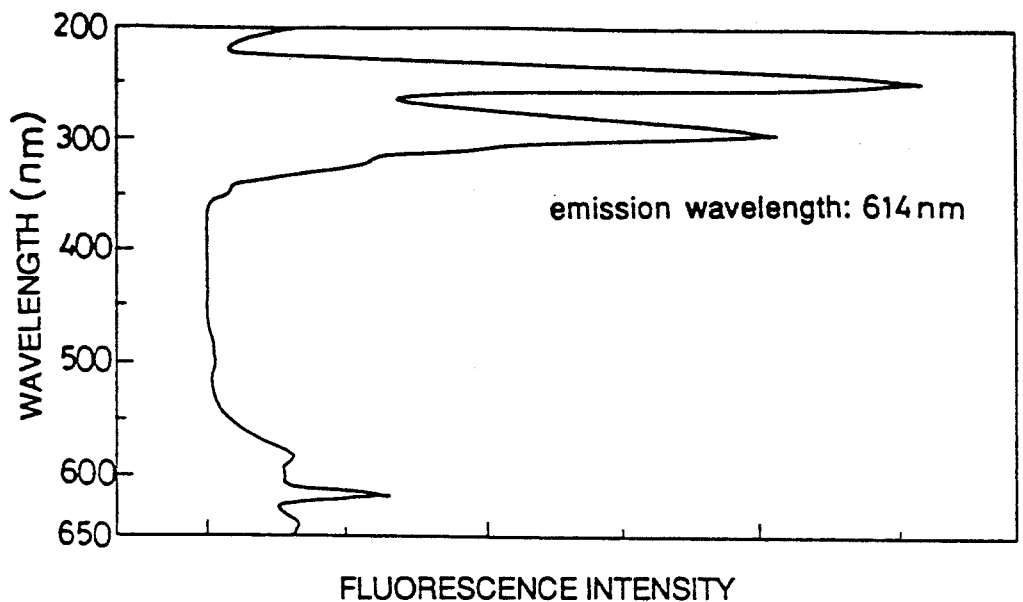
FIG. 6: The excitation spectrum of the complex formed from fluorescent compound (g) and europium ion described in Example 7.
Figure 7:
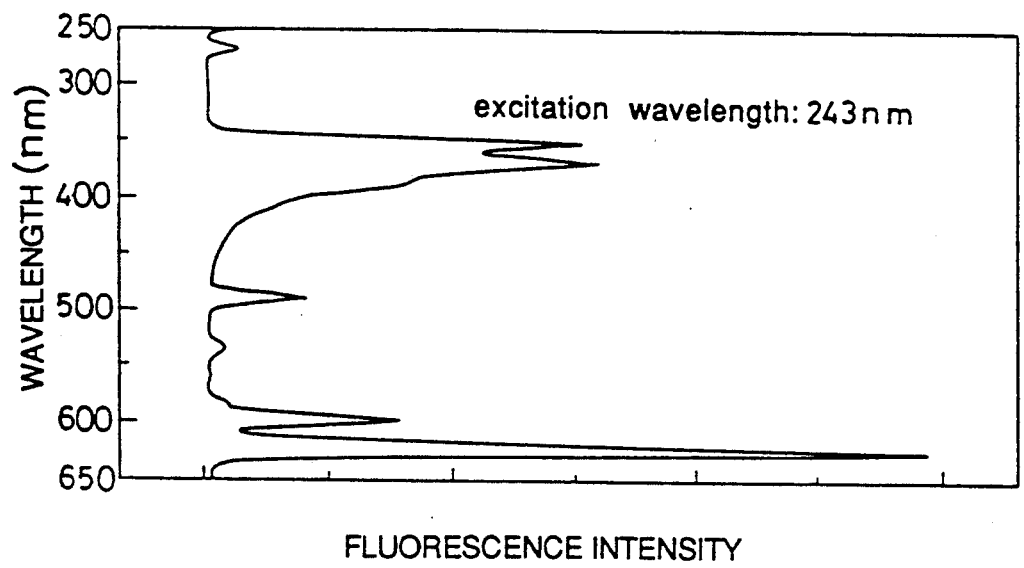
FIG. 7: The emission spectrum of the complex formed from fluorescent compound (g) and europium ion described in Example 7.

It was found that the optimum excitation wavelength under a emission wavelength at 614 nm was approximately 243 nm (FIG. 6), and the optimum emission wavelength under a excitation wavelength at 243 nm was approximately 619 nm (FIG. 7).

(3) Measurement of fluorescence lifetime of the europium complex

Figure 8:
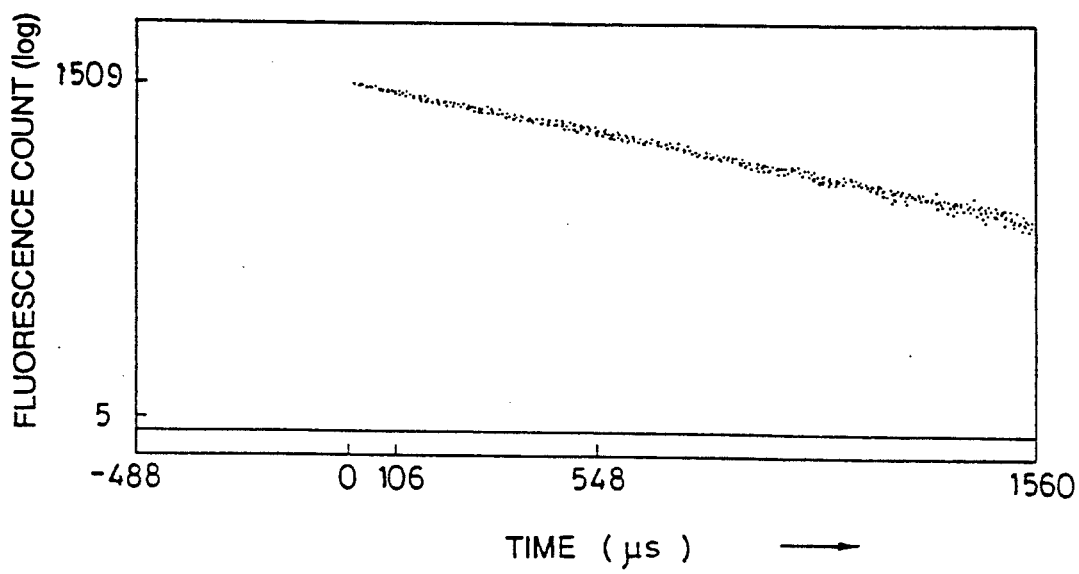
FIG. 8: The diagram of time-resolved fluorometric measurement of the complex formed from fluorescent compound (g) and europium ion described in Example 7.

Fluorescent compound (g) solution (80 μl) and europium chloride solution (80 μl) were mixed with 2 ml of 0.1 M sodium carbonate buffer (pH 10.5). Thirty minutes after the mixing, fluorescence lifetime of the mixed solution was measured. In this experiment, Nitrogen laser (NDL-100, Horiba, Ltd.) was used as a excitator, NAES-1100 (Horiba, Ltd.) and Universal Photon Counting System (Hamamatsu Photonics) were used to measure the fluorescence lifetime, and excitation and emission wavelength were set at 337.1 nm and 619 nm, respectively. The fluorescence lifetime of the europium complex was calculated to be 505 μs from the result described in FIG. 8.

(4) Effect of temperature on complexation time

Fluorescent compound (g) solution and europium chloride solution were diluted fifty-fold with 0.1 M sodium carbonate buffer (pH 10.5), respectively. Measurement of fluorescence intensity was started by adding 1.5 ml each of the diluted solutions simultaneously to a quartz cell set in JASCO FP-777 spectrofluorometer (described above). In this experiment, solution temperature was set at 25°, 30°, or 35° C.; fluorescence intensity was measured for 30 minutes, and excitation and emission wavelength were set at 242 nm and 619 nm, respectively.

Figure 9:
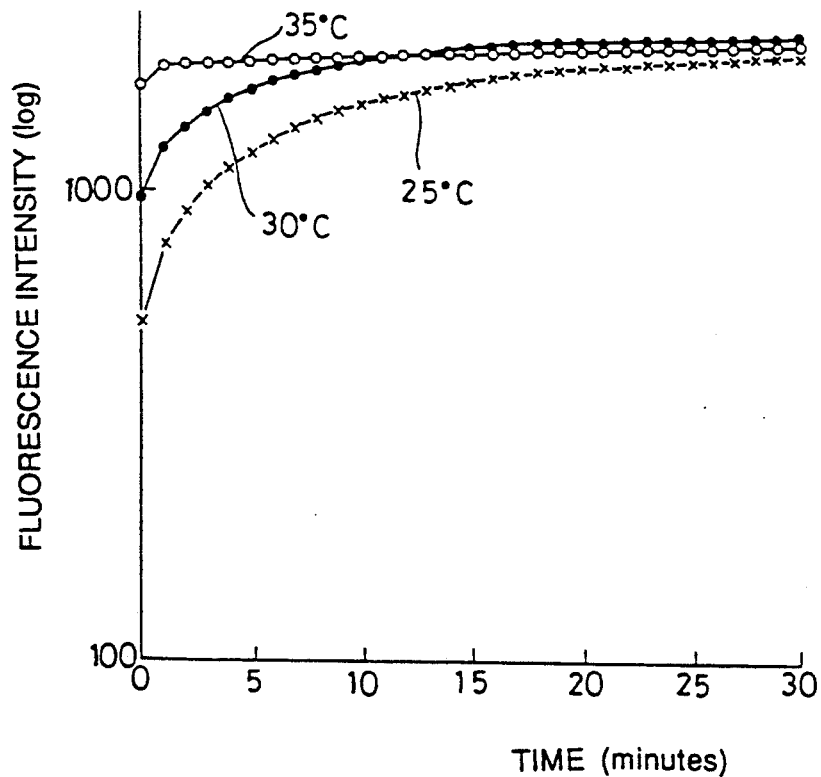
FIG. 9: The effect of temperature on the complex-forming time of fluorescent compound (g) and europium ion described in Example 7.

As shown in FIG. 9, the higher the solution temperature was, the sooner fluorescence intensity reached the maximum level, i.e. the sooner the complexation completed. Though the optimum complexation temperature was observed at 35° C., there was no problem to form the complex at room temperature, because fluorescence intensity reached to the maximum level in about 20 minutes even at room temperature (25° C.).

(5) Solubility of the europium complex in an aqueous solvent

Diluted solutions of fluorescent compound (g) $(0.001 \times 10^{-8}$ M to $250 \times 10^{-8}$ M) were prepared. Each one of the diluted solutions (30 μl) and europium chloride solution (30 μl) were mixed with 0.1 M sodium carbonate buffer (pH 10.5) (2.94 ml). Three hours after the mixing, fluorescence intensity of the sample solutions were measured by Arcus 1230 fluorometer (LKB-Wallac).

Figure 10:
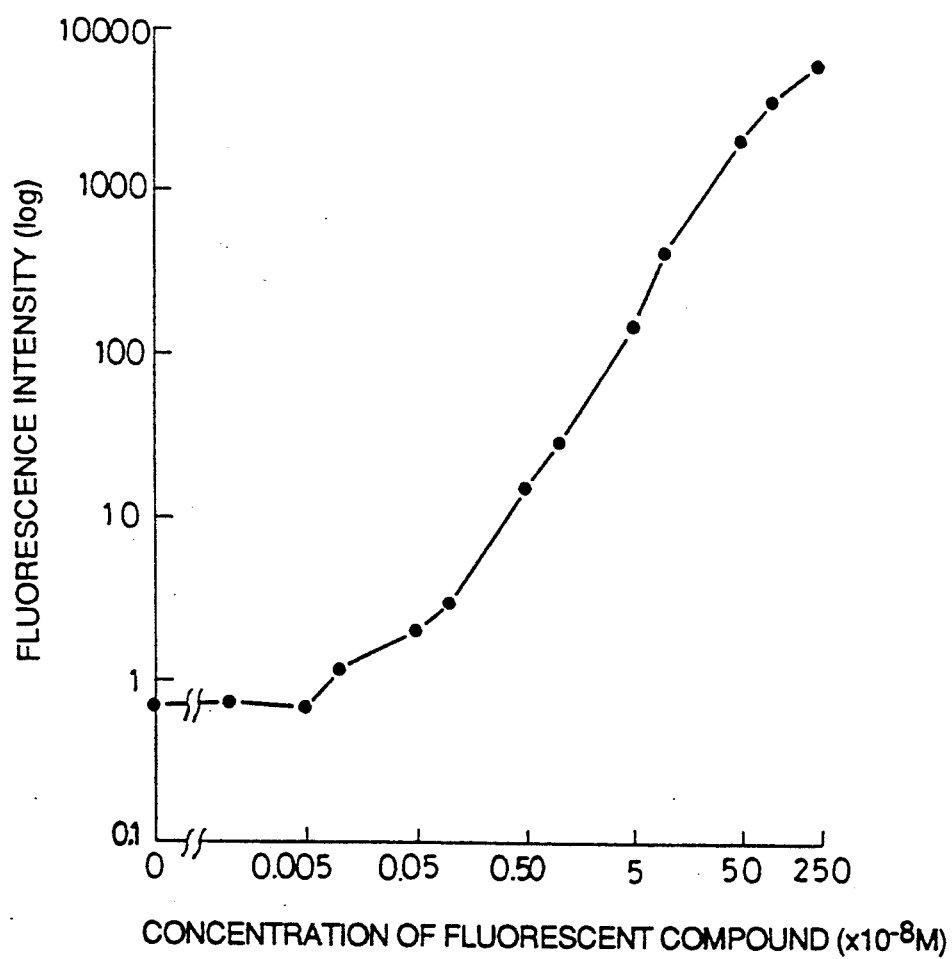
FIG. 10: Fluorescence emitted as a result of the complexation of fluorescent compound (g) and europium ion in aqueous solvent indicating the solubility of fluorescent compound (g) described in Example 7.

As shown in FIG. 10, a linearity between the fluorescence intensity and the compound concentration was observed in the concentration range of the fluorescent compound (g) between $0.1 \times 10^{-8}$ M and $250 \times 10^{-8}$ M.

EXAMPLE 8

Fluorescent characteristics of the europium complex of 7,10-diphenyl-2,15-diaza[3.3](2,9)-1,10-phenanthrolinophane-$N^2,N^{15}$-diacetic acid (u) and of 7,10-diphenyl-2,15-diaza[3.3](2,9)-1,10-phenanthrolinophane-$N^2,N^{15}$-diacetic acid, europium salt (PAPPA-Eu).

Figure 11:
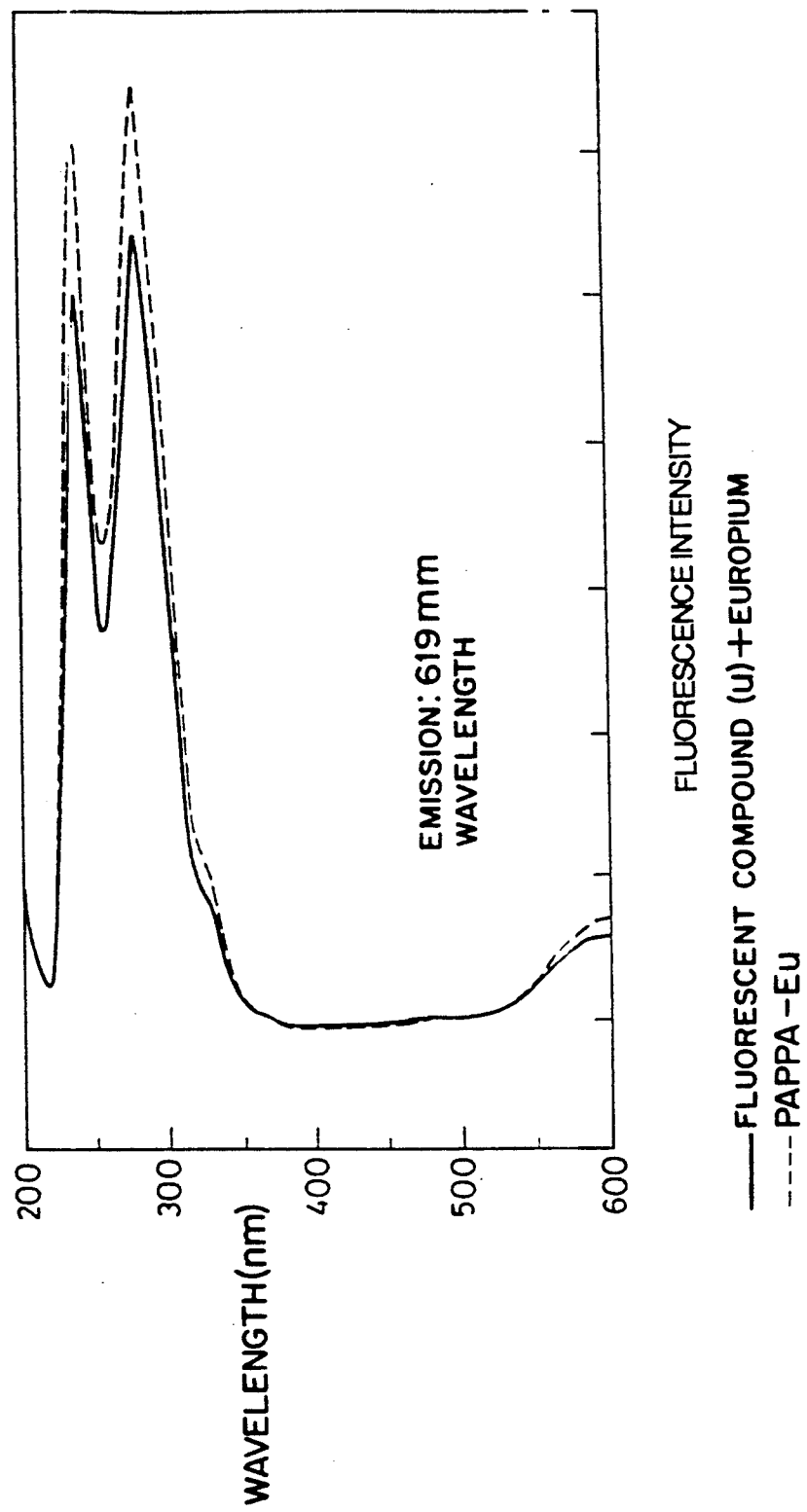
FIG. 11: Excitation spectra of the complex formed from fluorescent compound (u) and europium ion and that of PAPPA-Eu described in Example 8.
Figure 12:
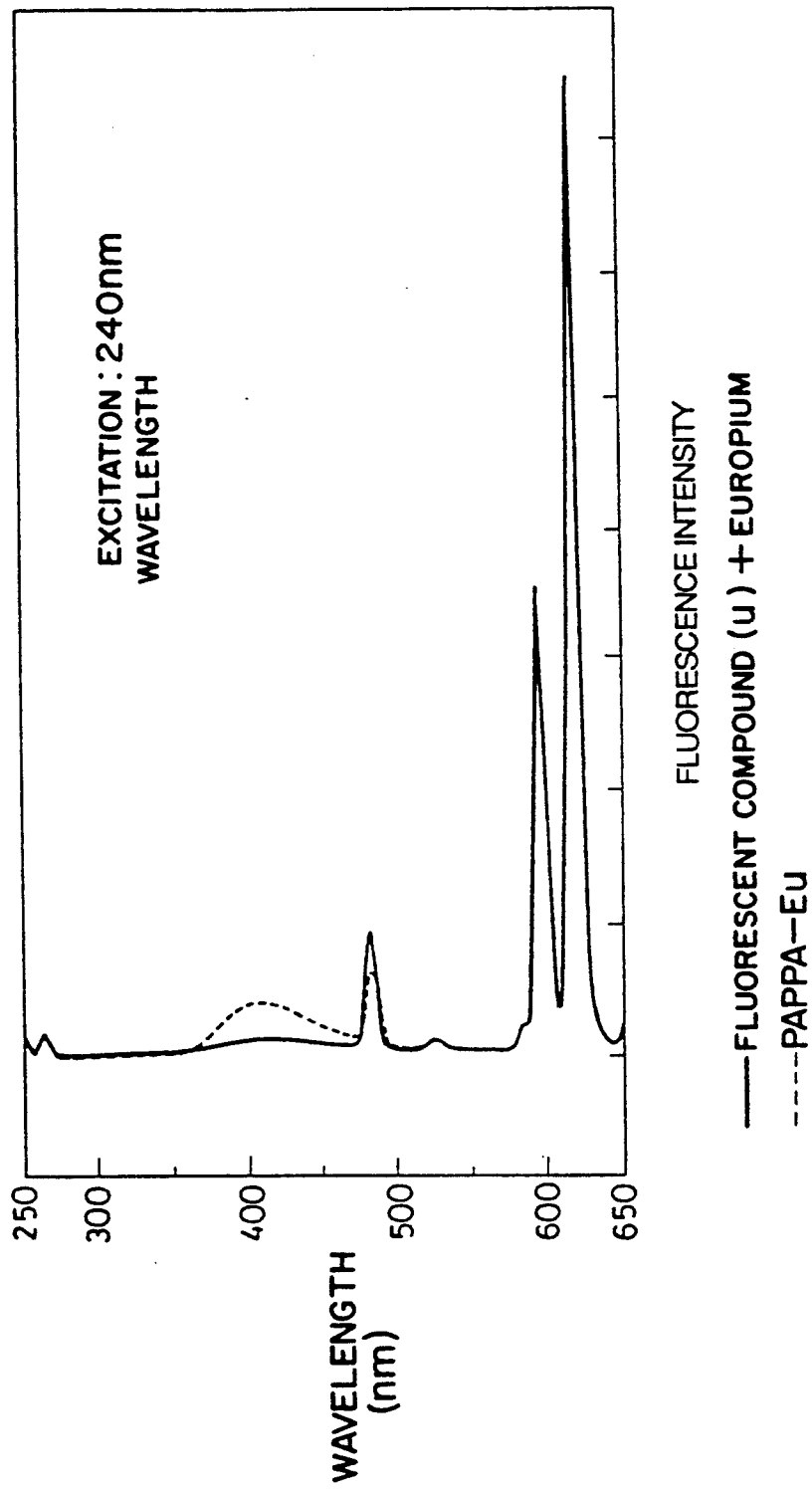
FIG. 12: Emission spectra of the complex formed from fluorescent compound (u) and europium ion and that of PAPPA-Eu described in Example 8.

(1) Measurement of excitation and emission spectra 7,10-diphenyl-2,15-diaza[3.3](2,9)-1,10-phenanthrolinophane-$N^2,N^{15}$-diacetic acid (u) (fluorescent compound (u)) synthesized in Example 4 was dissolved in 50% methanol/water to be $2.5 \times 10^{-4}$ M (fluorescent compound (u) solution). Fluorescent compound (u) solution (30 μl) and $2.5 \times 10^{-4}$ M europium chloride solution (30 μl) were mixed with 3.0 ml of 0.2 M sodium acetate buffer (pH 5.5). After 1 hour incubation of the mixed solution at 50° C., excitation and emission spectra were measured by FP-777 spectrofluorometer (described above). PAPPA-Eu synthesized in Example 6 was dissolved in 0.2 M Tris-acetate buffer (pH 9.0) at a concentration of $2.5 \times 10^{-6}$ M (PAPPA-Eu solution). Excitation and emission spectra of the solution were measured in the same manner as described above. Excitation and emission spectra were shown in FIG. 11 and 12, respectively. These results clearly showed that the spectrum patterns of europium complex of fluorescent compound (u) and PAPPA-Eu, which had been formed in synthetic steps, were almost same. Their fluorescence from europium ion were observed at 619 nm, which was identical to the europium complex of fluorescent compound (g) as described in Example 7.

(2) Measurement of fluorescence lifetime

Using the europium complex solution of fluorescent compound (u) and PAPPA-Eu solution prepared in Example 8(1), fluorescence lifetimes were measured by the same instruments as described in Example 7. The fluorescence lifetimes were calculated to be 1140 μs for the europium complex of fluorescent compound (u), and 1,180 μs for PAPPA-Eu. It was suggested that these fluorescence lifetimes were long enough to use for time-resolved fluoroassays.

EXAMPLE 9

Preparation of 7,10-bis(chlorosulfophenyl)-2,15-diaza[3.3](2,9)-1,10-phenanthrolinophane-$N^2,N^{15}$-diacetic acid(v)-labelled anti-hCG monoclonal antibody (1) Preparation of fluorescent compound (v)-labelled antibody (1)

Two-hundred μl of anti-hCG monoclonal antibody $(6 \times 10^{-5}$ M, HM21, Mochida Pharmaceutical Co., Ltd.) in 0.1 M sodium carbonate buffer (pH 9.1) was added to 0.5 mg $(5.5 \times 10^{-7}$ mol) of 7,10-bis(chlorosulfophenyl)-2,15-diaza[3.3](2,9)-1,10-phenanthrolinophane-$N^2,N^{15}$-diacetic acid (fluorescent compound (v)) synthesized in Example 4. The mixture was dissolved and incubated for 30 minutes at room temperature with stirring. Thereafter, the reaction solution was applied to a Sephadex G-50 column (Pharmacia) equilibrated with 0.1 M sodium carbonate buffer (pH 9.1) to remove unreacted fluorescent compound (v).

Figure 13:
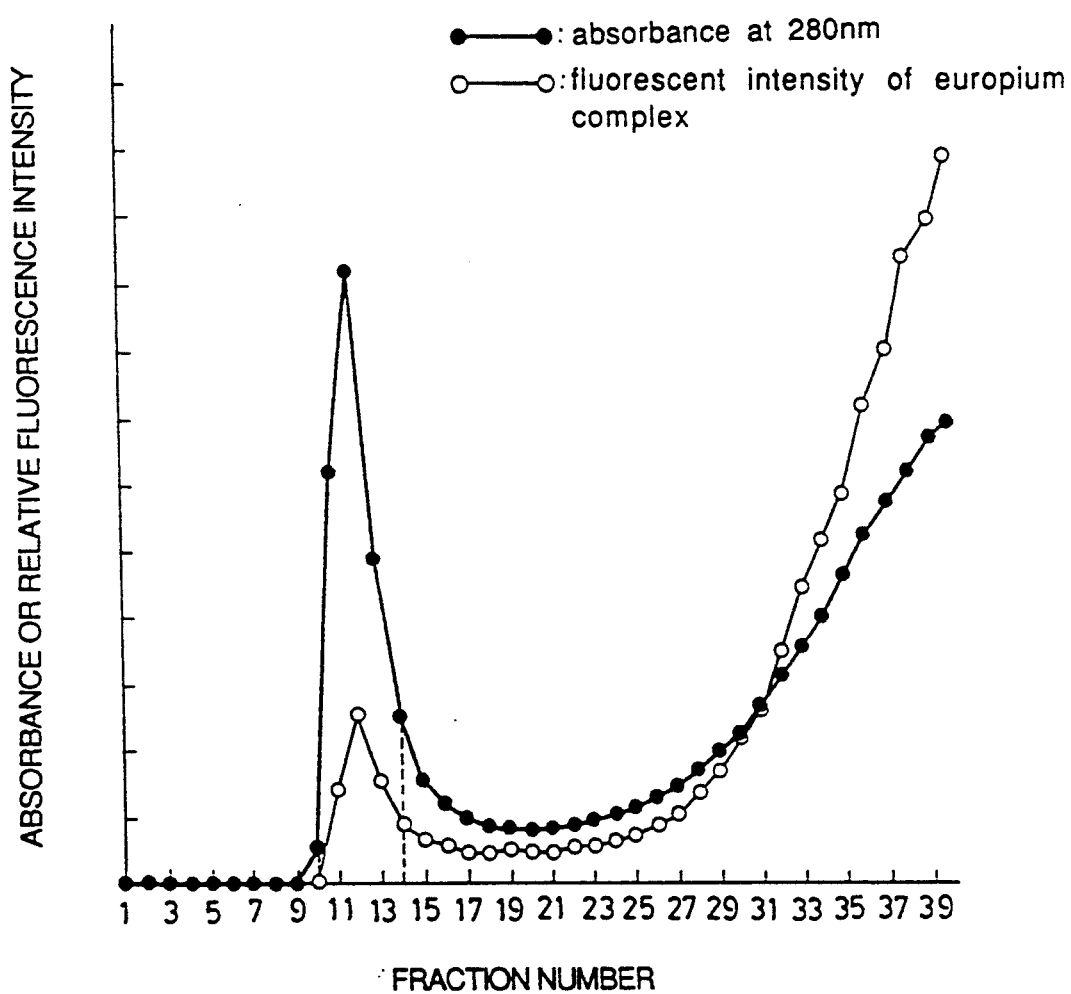
FIG. 13: The purification pattern of antibody labelled with fluorescent compound (v) described in Example 9.

The elution profile of the Sephadex G-50 column was shown in FIG. 13. The fluorescence peak was observed in void fractions, and this result indicated that the fluorescent compound (v)-labelled antibody (1) was formed. The void fractions with fluorescence activity were pooled, concentrated by Centricon (Amicon) and dialyzed against 50 mM Tris-HCl buffer (pH 7.2) containing 0.05% NaN$_3$ and 0.9% NaCl. The concentrations of fluorescent compound (v) and the antibody in the purified solution were calculated to be $7 \times 10^{-5}$ M and $1.2 \times 10^{-6}$ M, respectively, from the absorbances at 310 nm and 280 nm. Namely, one molecule of the antibody was labelled with 14 molecules of fluorescent compound (v).

(2) Preparation of fluorescent compound (v)-labelled antibody (2)

Fluorescent compound (v) was dissolved in dimetylformamide at a concentration of 60 mM. Ten μl of the fluorescent compound (v) solution was added to 0.2 ml of anti-hCG monoclonal antibody ($6 \times 10^{-5}$ M, HM21) in 0.1 M sodium carbonate buffer (pH 9.1), and the mixture was incubated for 30 minutes at room temperature with stirring. The purification of the fluorescent compound (v)-labelled antibody (2) was performed in the same manner as described in Example 9(1) The concentrations of fluorescent compound (v) and the antibody in the purified solution were calculated to be $1.0 \times 10^{-5}$ M and $1.0 \times 10^{-6}$ M, respectively, from the absorbances at 310 nm and 280 nm. Namely, one molecule of the antibody was labelled with 10 molecules of fluorescent compound (v).

(3) Preparation of rare-earth metal complex of fluorescent compound (v)-labelled antibody Both fluorescent compound (v) and europium chloride were dissolved in dimethylformamide at final concentrations of 60 mM and 120 mM, respectively. Thereafter, the europium complex of fluorescent compound (v) was formed by incubating the solution for 1 hour at room temperature. Ten μl of the europium complex of fluorescent compound (v) solution was added to 0.2 ml of anti-hCG monoclonal antibody ($6 \times 10^{-5}$ M, HM21) in 0.1 M sodium carbonate buffer pH 9.1), and the mixture was incubated for 30 minutes at room temperature with stirring. The purification of the europium complex of fluorescent compound (v)-labelled antibody was performed in the same manner as described in Example 9(1). The concentrations of the europium complex of fluorescent compound (v) and the antibody in the purified solution were calculated to be $2.1 \times 10^{-5}$ M and $1.5 \times 10^{-6}$ M, respectively, from the absorbances at 310 nm and 280 rm. Namely, one molecule of the antibody was labelled with 14 molecules of europium complex of fluorescent compound (v).

EXAMPLE 10

Preparation of 8-(3'-succinimidyloxycarbonylpropionamide)-2,15-diaza[3.3](2,9)-1,10-phenanthrolinophane-$N^2,N^{15}$-diacetic acid (p)-labelled anti-hCG monoclonal antibody and 7,10,20,23-tetrakis(chlorosulfophenyl)-2,15-diaza[3.3](2,9)-1,10-phenanthrolinophane-$N^2,N^{15}$-diacetic acid (γ)-labelled anti-hCG monoclonal antibody (1) Preparation of fluorescent compound (p)-labelled antibody 8-(3'-succinimidyloxycarbonylpropionamide)-2,15-diaza[3.3](2,9)-1,10-phenanthrolinophane-$N^2,N^{15}$-diacetic acid (p) (fluorescent compound (p)) synthesized in Example 2 was dissolved in ethanol at a concentration of 60 mM. Ten μl of the fluorescent compound (p) solution was added to 0.2 ml of anti-hCG monoclonal antibody ($6 \times 10^{-5}$ M, HM21) in 0.1 M sodium carbonate buffer (pH 9.1). The mixture was incubated for 30 minutes at room temperature with stirring. The purification of the fluorescent compound (p)-labelled antibody was performed in the same manner as described in Example 9(1). The concentrations of fluorescent compound (p) and the antibody in the purified solution were calculated to be $1.0 \times 10^{-5}$ M and $0.9 \times 10^{-6}$ M, respectively, from the absorbances at 310 nm and 280 nm. Namely, one molecule of the antibody was labelled with 11 molecules of fluorescent compound (p).

(2) Preparation of fluorescent compound (γ)-labelled antibody 7,10,20,23,-tetrakis(chlorosulfophenyl)-2,15-diaza[3.3](2,9)-1,10-phenanthrolinophane-$N^2,N^{15}$-diacetic acid (γ) (fluorescent compound (γ)) synthesized in Example 5 was dissolved in dimethylformamide at a concentration of 60 mM. Ten μl of the fluorescent compound (γ) solution was added to 0.2 ml of anti-hCG monoclonal antibody $6 \times 10^{-5}$ M, HM21) in 0.1 M sodium carbonate buffer (pH 9.1). The mixture was incubated for 30 minutes at room temperature with stirring. The purification of the fluorescent compound (γ)-labelled antibody was performed in the same manner as described in Example 9(1). The concentrations of fluorescent compound (γ) and the antibody in the purified solution were calculated to be $6.4 \times 10^{-6}$ M and $0.8 \times 10^{-6}$ M, respectively, from the absorbances at 310 nm and 280 nm. Namely, one molecule of the antibody was labelled with 8 molecules of fluorescent compound (γ).

EXAMPLE 11

Preparation of Fluorescent Compound (v)-Labelled Thyroxine

Fluorescent compound (v) synthesized in Example 4 was dissolved in dimethylformamide at a concentration of $5.0 \times 10^{-5}$ M, and thyroxine sodium salt was dissolved in ethanol at a concentration of $5.0 \times 10^{-5}$ M. The fluorescent compound (v) solution (100 μl) and the thyroxine sodium salt solution (100 μl) of ethanol were mixed and incubated for 30 minutes at room temperature with stirring. The resulting solution was subjected to a HPLC purification (column: AP-313, YMC Co., solvent: methanol: water=3:7(v:v) including 0.02% acetic acid) and the fluorescent compound (v)-labelled thyroxine was purified. The fluorescent compound (v)-labelled thyroxine was identified by measuring the thyroxine activity using an enzyme immunoassay (Boehringer Mannheim GmbH), and by measuring fluorescence intensity of the solution prepared by mixing equal volume of europium chloride ($1 \times 10^{-5}$ M) and the fraction.

EXAMPLE 12

Preparation of Fluorescent Compound (v)-Labelled Hepatitis B Surface Antigen

Two-hundred μl of hepatitis B surface (HBs) antigen derived from human plasma ($6 \times 10^{-5}$ M, Cheil Foods & Chemicals Inc.) in 0.1 M sodium carbonate buffer (pH 9.1) was added to 0.5 mg of fluorescent compound (v) synthesized in Example 4. The mixture was dissolved and incubated for 30 minutes at room temperature with stirring. The purification of the fluorescent compound (v)-labelled HBs antigen was performed in the same manner as described in Example 9(1). The concentrations of fluorescent compound (v) and the HBs antigen were calculated to be $4.8 \times 10^{-6}$ M and $1.2 \times 10^{-6}$ M, respectively, from the absorbances at 310 nm and 280 nm. Namely, one molecule of HBs antigen was labelled with 4 molecules of fluorescent compound (v).

EXAMPLE 13

Preparation of Fluorescent Compound (v)-Labelled Oligomer Probe of Hepatitis B Virus Fluorescent compound (v) synthesized in Example 4 was dissolved in dimethylformamide at a concentration of 100 mM. An oligomer probe complementary to the hepatitis B virus DNA (position of core antigen DNA 1941-1970, 30 mer) was synthesized using a DNA synthesizer (Applied Biosystems, Inc., Model 381A), and an amine linker-arm was automatically coupled to the 5' end of the probe using Aminolink 2 (Applied Biosystems, Inc.). The oligomer was then cleaved from the solid support, deprotected by ordinary methods, and desalted with ethanol precipitation. Thereafter, 40 μg of the oligomer was dissolved in 80 μl of 0.1 M sodium carbonate buffer (pH 9.0), and 24 μl of fluorescent compound (v) solution (100 mM) was added. The mixture was incubated for 30 minutes at room temperature. After the reaction, in order to remove the unreacted fluorescent compound (v), the mixture was applied to a Sephadex G-25 column (Pharmacia) equilibrated with 50 mM triethylamine acetate buffer (TEAA). The void fractions were pooled and concentrated by Centricon 3 (Amicon). The concentrated sample was injected to a C8 reverse-phase column (Aquapore RP300 C8, Applied Biosystems, Inc.) and eluted with a linear gradient from 15% to 30% acetonitrile in 50 mM TEAA. The absorbance at 260 nm and the fluorescence intensity of each fraction were measured, and the fractions which showed both activity were pooled. The pooled fraction was dried in reduced pressure and then dissolved in 0.1 M Tris-HCl buffer (pH 8.0) containing 1 mM ethylenediamine tetraacetic acid (EDTA) to be a concentration of 5 μg/ml.

EXAMPLE 14

Preparation of Fluorescent Compound (v)-Labelled Streptavidin

Fluorescent compound (v) (0.5 mg) synthesized in Example 4 was dissolved in 0.2 ml of streptavidin (Sigma Chemical Company) solution ($6 \times 10^{-5}$ M) prepared with 0.1 M sodium carbonate buffer (pH 9.1), and then the mixture was incubated for 30 minutes at room temperature with stirring. The fluorescent compound (v)-labelled streptavidin was purified according to the method described in Example 9(1). The concentrations of fluorescent compound (v) and streptavidin in the purified solution were calculated to be $1.3 \times 10^{-5}$ M and $1.4 \times 10^{-6}$ M, respectively, from the absorbances at 310 nm and 280 nm. Namely, one molecule of streptavidin was labelled with 9 molecules of fluorescent compound (v).

EXAMPLE 15

Preparation of Antibody Conjugated to Bovine Serum Albumin Labelled with Fluorescent Compound (v)

(1) Preparation of fluorescent compound (v)-labelled bovine serum albumin

Fluorescent compound (v) (2.5 mg) synthesized in Example 4 was dissolved in 1 ml of bovine serum albumin (BSA) solution ($6 \times 10^{-5}$ M) prepared with 0.1 M sodium carbonate buffer (pH 9.1), and then the mixture was incubated for 30 minutes at room temperature with stirring. The fluorescent compound (v)-labelled BSA was purified according to the method described in Example 9(1). In the purified solution of the fluorescent compound (v)-labelled BSA, $8.4 \times 10^{-5}$ M of fluorescent compound (v) and $7.0 \times 10^{-6}$ M of BSA were determined by Protein assay (Biorad Laboratories, Inc.) and by measuring the absorbance at 310 nm, respectively. Namely, one molecule of BSA was labelled with 12 molecules of fluorescent compound (v).

(2) Incorporation of maleimide groups to fluorescent compound (v)-labelled BSA

The fluorescent compound (v)-labelled BSA was dialyzed against 50 mM phosphate buffer (pH 7.0) and concentrated. One ml of the fluorescent compound (v)-labelled BSA solution ($3 \times 10^{-5}$ M) and 100 μl of 18 mM sulfosuccinimidyl-4-(N-maleimidomethyl)cyclohexane-1-carboxylate (sulfo-SMCC, Pierce) dissolved in the same buffer were mixed and incubated for 1 hour at room temperature. The maleimide groups-incorporated BSA labelled with fluorescent compound (v) was purified by a gel filtration column of Sephadex G-25 equilibrated with 0.1 M phosphate buffer (pH 6.2), and the purified fractions were pooled and concentrated by Centricon (Amicon). The number of incorporated maleimide groups were determined by the method of Ishikawa et al. (J. Immunoassay, 4(3), 209-327 (1983)). Five maleimide groups per BSA molecule were incorporated.

(3) Incorporation of mercapto groups to antibody

A solution of anti-hCG monoclonal antibody (HM21) was prepared with 0.1 M sodium carbonate buffer (pH 9.1) at a concentration of $3 \times 10^{-5}$ M. The antibody was derivatized with N succinimidyl-S-acetylthioacetate (SATA, 15 mM, Calbiochem Boehring, Inc.) in dimethylformamide (10 μl); the SATA solution was added in four portions to the stirring HM21 solution (1 ml) at one-minute interval, and the mixture was incubated for 1 hour at room temperature. The derivatized antibody was dialyzed against 0.1 M phosphate buffer (pH 6.2) and concentrated. Three mercapto groups per antibody molecule were determined by the method of Ishikawa et al. (J. Immunoassay, 4(3), 209-327 (1983)).

(4) Preparation of antibody conjugated to BSA labelled with fluorescent compound (v)

Four-hundred μl of the maleimide groups-incorporated BSA labelled with fluorescent compound (v) solution (see Example 15(2)) and 300 μl of the mercapto groups-incorporated antibody solution (see Example 15(3)) were mixed and concentrated to a volume of 300 μl in an atmosphere of nitrogen. The solution was purged with nitrogen gas and mixed with 50 μl of hydroxylamine (0.5 M, pH 7.0). The mixture was incubated for 2 hours at 37° C. in the atmosphere of nitrogen. After the incubation, 20 μl of 2-mercaptoethanol (0.12 M) was added, and the mixture was incubated for 15 minutes at room temperature. Subsequently, 20 μl of N-ethylmaleimide (0.24 M) was added, and the mixture was incubated for another 15 minutes at room temperature. The resulting mixture was subjected to an Ultrogel AcA34 (IBF Biotechnics) column chromatography, and the fractions, including the conjugate of maleimide groups-incorporated BSA labelled with fluorescent compound (v) and the mercapto groups-incorporated antibody, were collected. The conjugate was identified by measuring the antibody activity and the fluorescent intensity. The antibody activity of the fractions was determined as competitive activity using an enzyme immunoassay kit for hCG (Mochida Pharmaceutical Co., Ltd.), and the fluorescence intensity was measured in the presence of europium chloride ($1 \times 10^{-5}$ M).

EXAMPLE 16

A time-resolved fluoroimmunoassay for hCG using fluorescent compound (v) or rare-earth metal complex of fluorescent compound (v) as a label Two-hundred µl/well of anti-hCG monoclonal antibody (10 µg/ml, HM70, Mochida Pharmaceutical Co., Ltd.) in 0.1 M sodium carbonate buffer (pH 9.6) was immobilized to the wells of 96-well microplates (EFLAB, Inc.) for 1 hour at 37° C. After washing with deionized water, the wells were blocked with 0.5% BSA containing 0.05% NaN3 (300 µl/well) in 0.1 M sodium carbonate buffer (pH 8.3) for more than 2 hours at room temperature. These wells were stored in a refrigerator until use.

Figure 14:
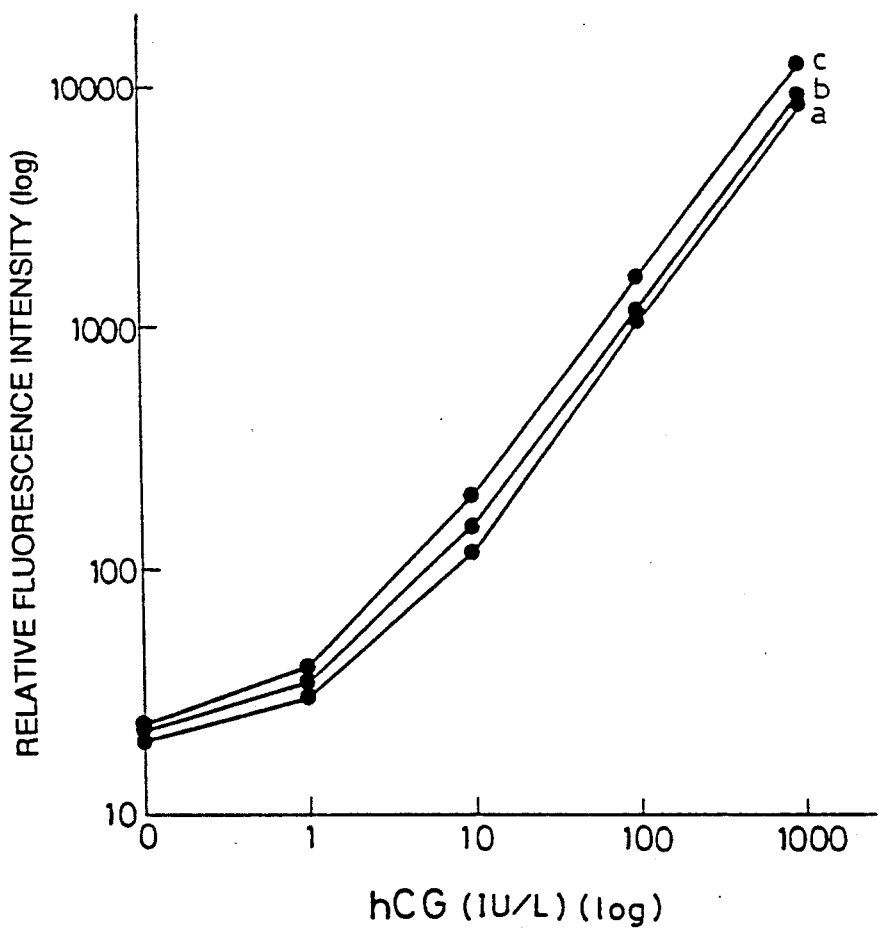
FIG. 14: The time-resolved fluoroimmunoassay for hCG as described in Example 16.

After washing with deionized water, 100 µl/well of hCG standard (1st IRP, 75/537) diluted with normal rabbit serum (NRS) and 100 µl/well of assay buffer (50 mM Tris-HCl (pH 7.8) containing 0.9% NaCl, 0.5% BSA, 0.05% bovine gamma globulin, and 0.01% Tween 40) were added to the antibody-immobilized wells and incubated for 1 hour at room temperature. After washing 5 times with saline containing 0.005% Tween 20 (wash solution), 200 µl/well of the fluorescent compound (v)-labelled antibody (1) (0.5 µg/ml, see Example 9), or -labelled antibody (2) (0.7 µg/ml, see Example 9) in assay buffer containing $1 \times 10^{-5}$ M EuCl$_3$ was added to the wells and incubated for 1 hour at room temperature. In the case of employing the rare-earth metal complex of fluorescent compound (v)-labelled antibody (see Example 9), the complex-labelled antibody was diluted at a concentration of 0.3 µg/ml with assay buffer, and incubated as described above. The wells were washed with wash solution to remove the unreacted labelled antibody, and then the time-resolved fluorescence of the wells were measured by Arcus 1230 fluorometer (LKB-Wallac). The reactivity in a time-resolved fluoroimmunoassay (TR-FIA) for hCG was not influenced by the difference of labelling method (FIG. 14). Also, the reactivity in the TR-FIA for hCG was not influenced by the difference that complex formation was carried out during labelling, or during immunoreaction (FIG. 14). Moreover, these TR-FIAs could detect the antigen with high sensitivity.

EXAMPLE 17

TR-FIAs for hCG Using Fluorescent Compound (p) and (γ) as Labels

Figure 15:
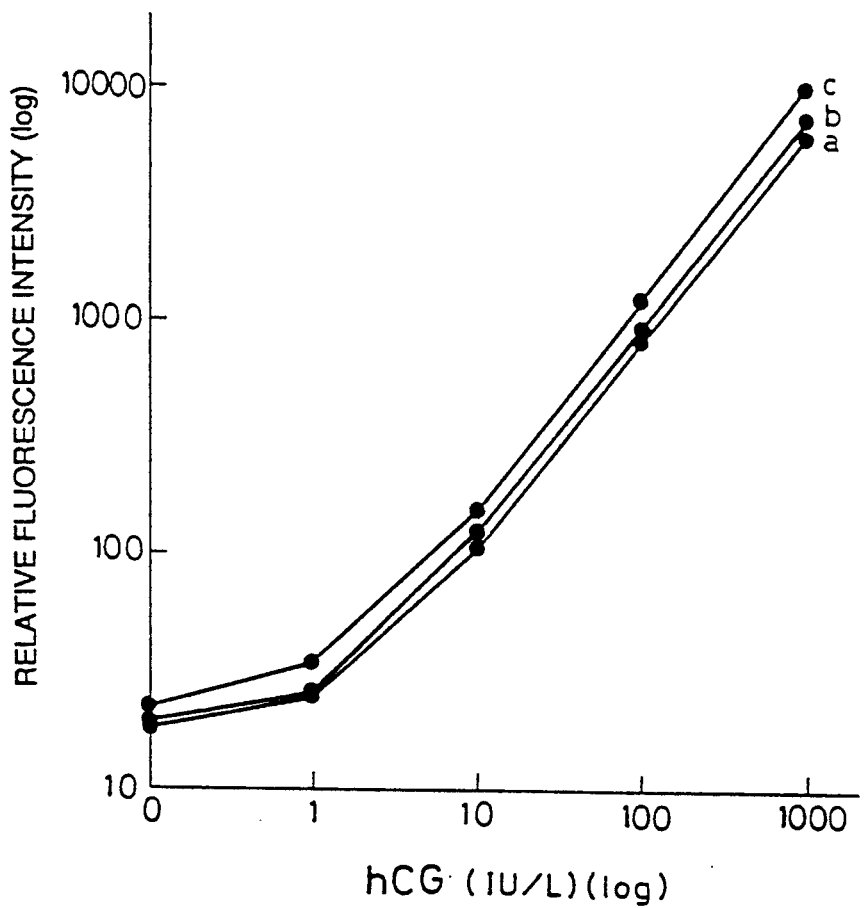
FIG. 15: The time-resolved fluoroimmunoassay for hCG as described in Example 17.

Each of the fluorescent compound (p)-labelled antibody (see Example 10) and the fluorescent compound (γ)-labelled antibody (see Example 10) was diluted separately at a concentration of 0.8 µg/ml and 1.2 µg/ml, respectively, with assay buffer containing europium chloride ($1 \times 10^{-5}$ M). The procedure of the TR-FIA for hCG were the same as described in Example 16 except the use of these labelled antibodies. It was shown in FIG. 15 that the reactivity of the TR-FIA using the fluorescent compound (p)-labelled antibody or the fluorescent compound (γ)-labelled antibody was almost same as that obtained using the fluorescent compound (v)-labelled antibody (Example 16). It was also shown that the TR-FIAs using fluorescent compound (p) and (γ) as labels were as highly sensitive as that using fluorescent compound (v) as a label.

EXAMPLE 18

A TR-FIA for Thyroxine Using Fluorescent Compound (v) as a Label

Two-hundred µl/well of anti-thyroxine monoclonal antibody (067-A2203, Biospacific, Inc., 10 µg/ml) in 0.1 M sodium carbonate buffer (pH 9.6) was immobilized to the wells of 96-well microplates for 1 hour at 37° C. The wells were washed with deionized water and blocked with 0.5% BSA containing 0.05% NaN3 in 0.1 M sodium carbonate buffer (pH 8.3) for more than 2 hours at room temperature. These antibody-immobilized wells were stored in a refrigerator until use.

Figure 16:
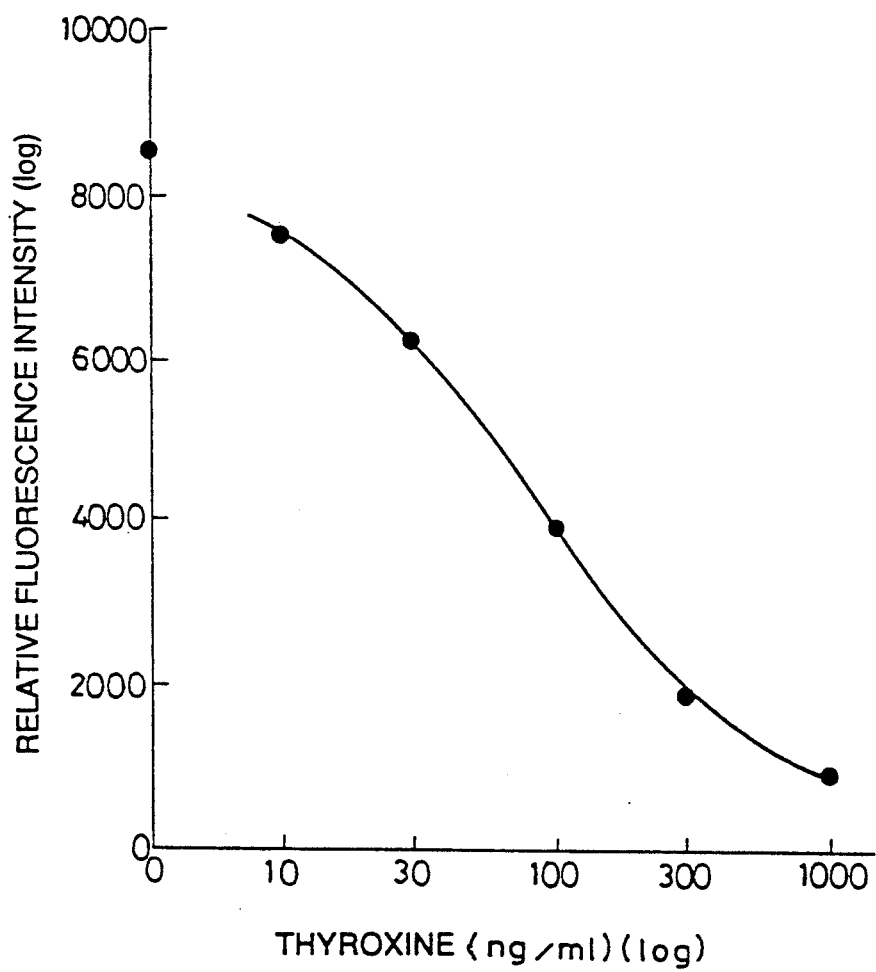
FIG. 16: The time-resolved fluoroimmunoassay for thyroxine as described in Example 18.

After washing the wells with deionized water, 50 µl/well of thyroxine standard in NRS treated with charcoal and 150 µl of the fluorescent compound (v)-labelled thyroxine (see Example 11) in assay buffer were added and incubated with the wells for 1 hour at room temperature. The wells were washed with wash solution to remove the unreacted labelled thyroxine. Two-hundred µl/well of europium chloride ($2 \times 10^{-6}$ M) in 0.2 M Tris-acetate buffer (pH 9.0) was added to the washed wells and incubated for 1 hour at room temperature. The time-resolved fluorescence of the wells were measured by Arcus 1230 fluorometer. A standard curve was shown in FIG. 16, from which the detection limit was calculated to be 5 ng/ml.

EXAMPLE 19

A TR-FIA for Detection of Antibody to HBs Antigen Using Fluorescent Compound (v) as a Label Two-hundred µl/well of HBs antigen (10 µg/ml) prepared from human plasma in 0.1 M sodium carbonate buffer (pH 9.6) was immobilized to the wells of 96-well microplates for 1 hour at 37° C. The wells were washed with deionized water and blocked with 0.5% BSA containing 0.05% NaN3 in 0.1 M sodium carbonate buffer (pH 8.3) for more than 2 hours at room temperature. These HBs antigen immobilized wells were stored in a refrigerator until use.

After washing the wells with deionized water, 50 µl/well of control sera (positive and negative) or sample sera, and 150 µl/well of assay buffer were added and incubated with the wells for 1 hour at room temperature. The wells were washed with wash solution, and then incubated with 200 µl/well of the fluorescent compound (v)-labelled HBs antigen (1 µg/ml, see Example 12) in assay buffer containing europium chloride ($1 \times 10^{-5}$ M). The wells were washed with wash solution to remove the unreacted labelled antigen. The time-resolved fluorescence of the wells were measured by Arcus 1230 fluorometer. It was shown in Table 1 that 28 sera out of 100 sera were positive in this assay, and that 26 sera were positive in the assay using a commercially available enzyme immunoassay kit (ELSIA anti-HBs, International Reagent Corporation). Thus, it was demonstrated that this TR-FIA was more sensitive to detect HBs antigen than the commercially available method.

TABLE 1

| DETECTION OF ANTIBODY TO HBs ANTIGEN | | | |
|---|---|---|---|
| | TR-FIA in Ex. 19 | | |
| | + | − | Total |
| commercially avail- + | 26 | 0 | 26 |

TABLE 1-continued

DETECTION OF ANTIBODY TO HBs ANTIGEN

TR-FIA in Ex. 19

|  | + | − | Total |
|---|---|---|---|
| able kit | — | 2 | 72 | 74 |
| Total | | 28 | 72 | 100 |

EXAMPLE 20

Figure 17:
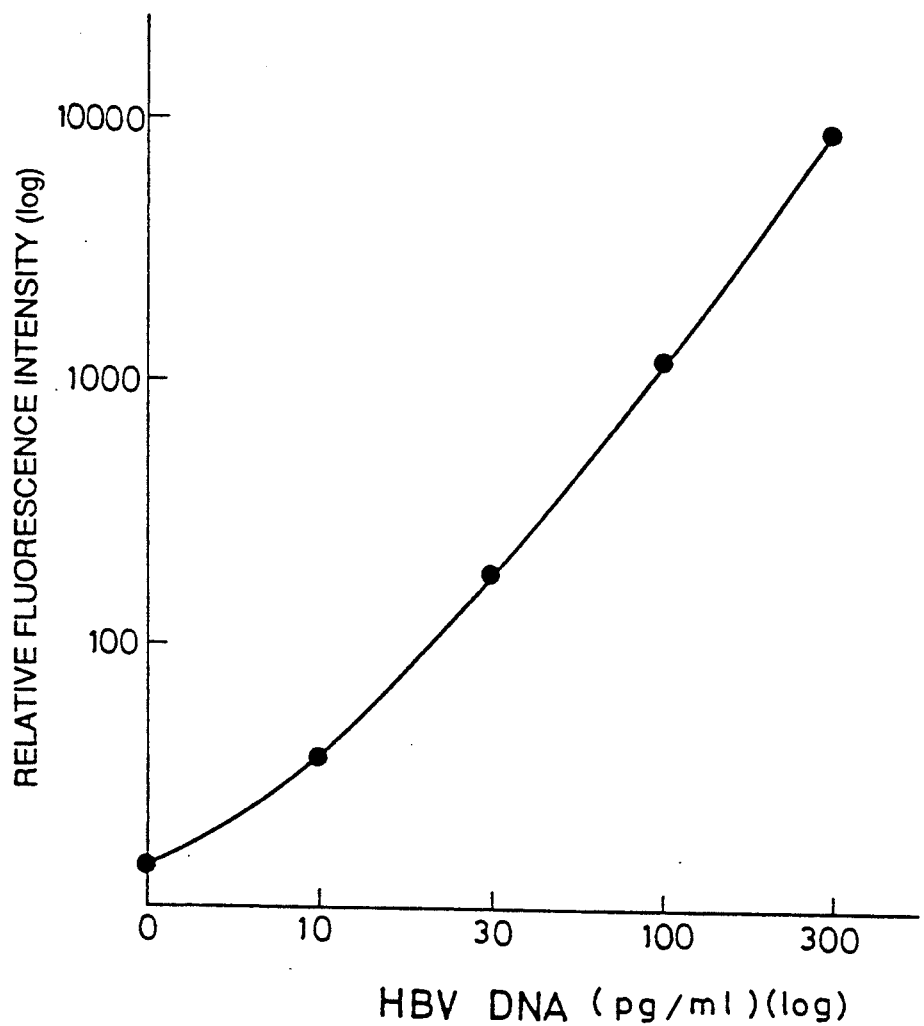
FIG. 17: The time-resolved fluorescent probe assay for HBV-DNA as described in Example 20.
Figure 18:
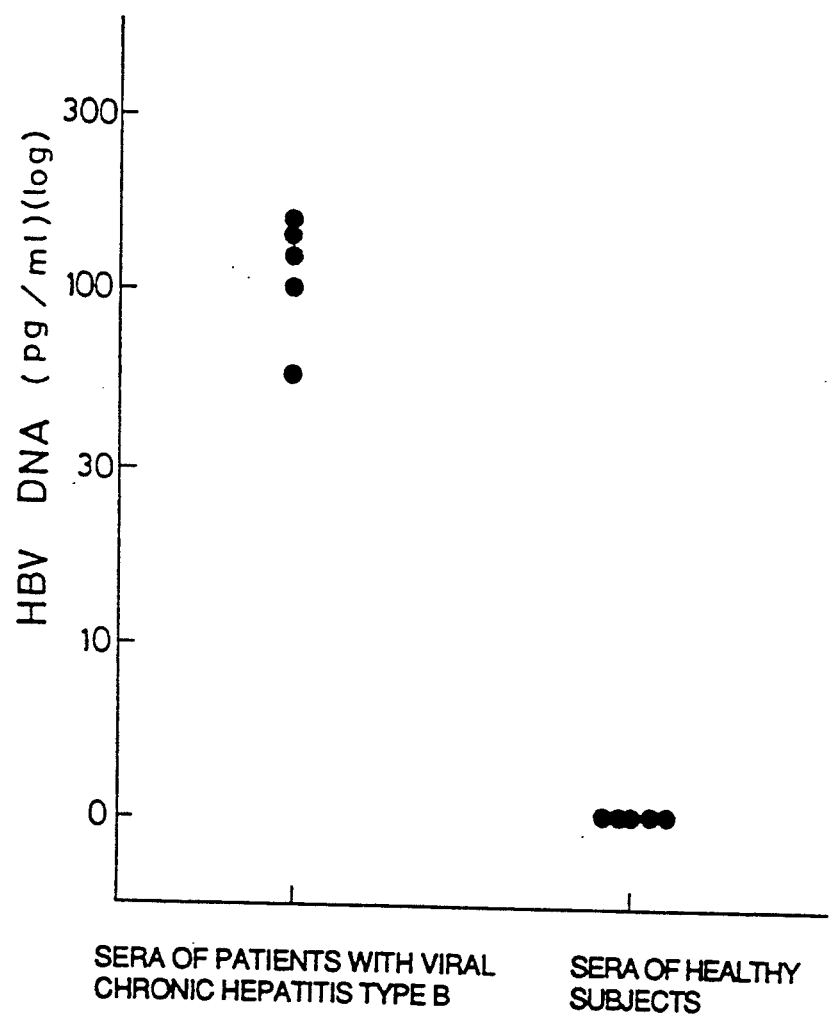
FIG. 18: HBV-DNA levels measured by the time-resolved fluorescent probe assay in the type B-hepatitis patients and healthy subjects as described in Example 20.

A DNA Probe Assay for Hepatitis B Virus Using Fluorescent Compound (v) as a Label A serum of patient with viral chronic hepatitis type B, at a concentration of 1325 pg/ml of hepatitis B virus-DNA, was diluted stepwise with normal sera to use as samples. One-hundred μl of each samples was digested with 10 μl of proteinase K (5 mg/ml) in 50 mM acetate buffer (pH 6.5) containing 1% sodium dodecylsulfate (SDS) and 5 mM EDTA for 1 hour at 68° C. According to usual method, the reaction mixtures were extracted twice with phenol/chloroform. The extracted samples were then heat-denatured (95° C., 10 minutes), and immobilized to the wells of 96-well microplates. Fluorescent compound (v)-labelled oligomer probe was adjusted to 50 ng/ml with the hybridization solution (6×SSC (standard saline citrate), 5×Denhard's, 0.1% SDS, 100 μg/ml denatured salmon sperm DNA, and $1\times10^{-5}$ M EuCl$_3$ at final concentration). Two-hundred μl/well of this solution was added and incubated with the wells for 3 hours at 55° C. After the incubation, the wells were then washed 5 times with 2×SSC containing 0.1% SDS for 5 minutes at room temperature to remove the unreacted probe. The time-resolved fluorescence of the washed wells were measured by Arcus 1230 fluorometer. It was indicated that this assay was capable of detecting 1 pg/ml of hepatitis B virus-DNA (FIG. 17). From results of the measurement for 5 sera of patients with viral chronic hepatitis type B and 5 sera of healthy subjects, it was also demonstrated that an apparent difference existed in the serum levels of hepatitis B virus-DNA between these two groups (FIG. 18).

EXAMPLE 21

Figure 19:
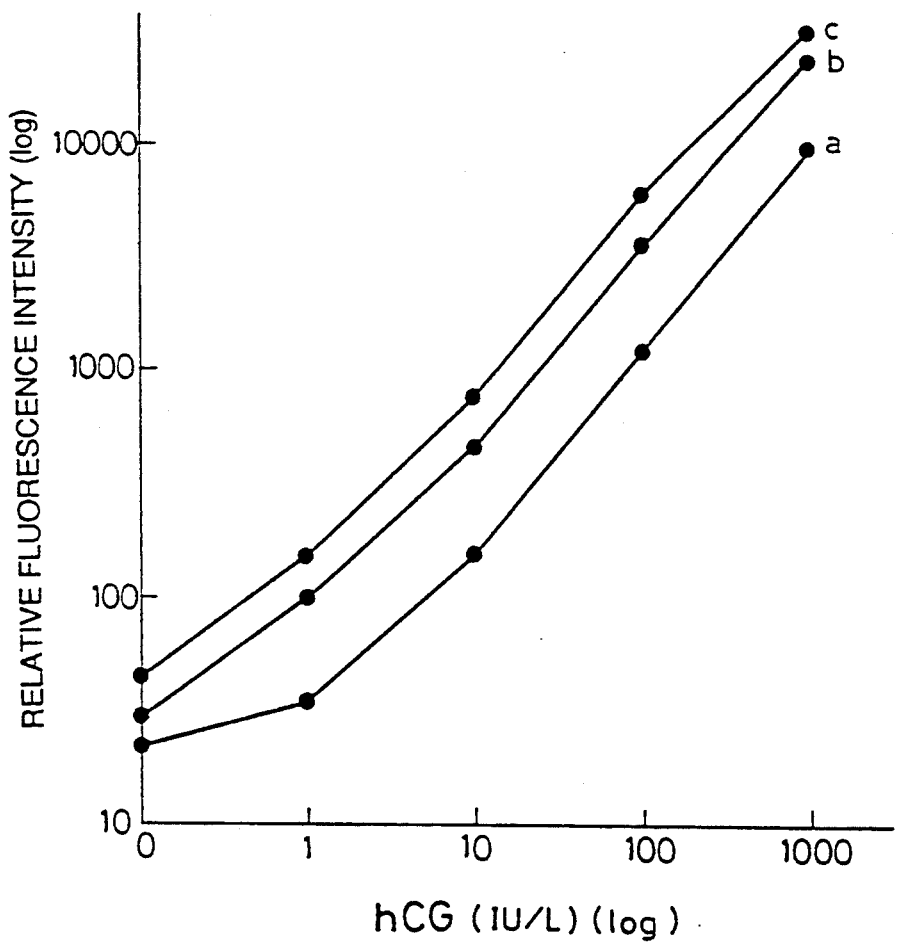
FIG. 19: The amplified time-resolved fluoroimmunoassay for hCG using the fluorescent compound-labelled intermediates as described in Example 21 and 22.

An Amplified TR-FIA for hCG Using the Fluorescent Compound (v)-Labelled Streptavidin The procedure for preparation of anti-hCG monoclonal antibody-immobilized wells and for blocking were same as described in Example 16. After washing the wells with deionized water, 50 μl/well of hCG standard (1st IRP, 75/537) diluted with NRS and 150 μl/well of assay buffer were added and incubated for 1 hour at room temperature. After washing with wash solution, 100 μl/well of biotinylated anti-hCG antibody (HM21), which was diluted to be 2 μg/ml with assay buffer, was added and incubated with the antigen captured wells for 1 hour at room temperature. The biotinylated antibody was prepared by the method of Diamandis et al. (Anal. Chem., 61, 48–53 (1989)). After washing the wells with wash solution, 100 μl/well of the fluorescent compound (v)-labelled streptavidin (0.5 μg/ml) in assay buffer containing $1\times10^{-5}$ M Eucl$_3$ was added and incubated for 1 hour at room temperature. After washing with wash solution, the time-resolved fluorescence of the wells were measured by Arcus 1230 fluorometer. It was indicated in FIG. 19 that this amplification method using biotin-streptavidin system was capable of increasing the sensitivity about 3-fold in comparison with the ordinary method (Example 16).

EXAMPLE 22

An Amplified TR-FIA for hCG Using the Antibody Conjugated to BSA Labelled with Fluorescent Compound (v)

In this assay, the conditions were same as described in Example 16 except that the antibody conjugated to BSA labelled with fluorescent compound (v) (1.5 μg/ml) prepared in Example 15 was used instead of the fluorescent compound (v)-labelled antibody. This amplification method could increase the sensitivity about 5-fold in comparison with the ordinary method described in Example 16.

By this invention, the fluorescent compound, complex, reagent, and specific binding assay, of which characteristics are described below, are offered.

That is:

The fluorescent compound of this invention forms a stable complex with rare-earth metal ion, since it possesses the ring structure whose cavity size fits the ion radius of rare-earth metal.

The fluorescent compound of this invention including a carboxyl group forms a very stable complex due to the quatorial coordination of the ring nitrogens and, in addition, the axial coordination of the carboxyl group which has a high affinity to rare-earth metal ion.

The fluorescent compound of this invention bearing the carboxyl group is water-soluble.

The fluorescent compound of this invention bearing the carboxyl group is not susceptible to oxidation under any pH condition and permits the maintenance of the stable state.

The fluorescent compound of this invention is stable even in aqueous solutions and the complex formed from said fluorescent compound and rare-earth metal ion is hardly liable to the quenching of fluorescence with water, since the hydrophobic environment around the metal ion become readily formed.

The fluorescent compound of this invention possesses the functional groups capable of binding to specific binding agent, the presence of which does not affect fluorescence characteristics.

The fluorescent compound of this invention, has two phenanthroline rings in its structure, that is, one rare-earth metal ion is coordinated by two phenanthroline rings. Hence, the amount of the excitation energy transferred to a rare-earth metal ion is enhanced to afford a large fluorescence intensity.

The fluorescence lifetime derived from the complex of this invention is satisfactorily longer compared with that of the background fluorescence. Accordingly, the measurement of the fluorescence intensity without being affected by the background is assured by measuring the fluorescence intensity after the background fluorescence has disappeared (time-resolved fluorescent assay).

As the reagent of this invention possesses various properties such as the characteristics of preceding fluorescent compound or complex of this invention, and the activity and bonding property of the specific binding agent, to which said fluorescent compound or complex bonded, the immunoassay with a high sensitivity and without danger becomes possible by using the reagent of this invention.

The specific binding assay of this invention can be carried out by simply replacing the conventional labelled reagents in the enzyme immunoassay with the reagent of this invention, and high sensitivities which have not been so far achieved can be attained by this invention.

What is claimed is:

1. A fluorescent compound expressed by formula A:

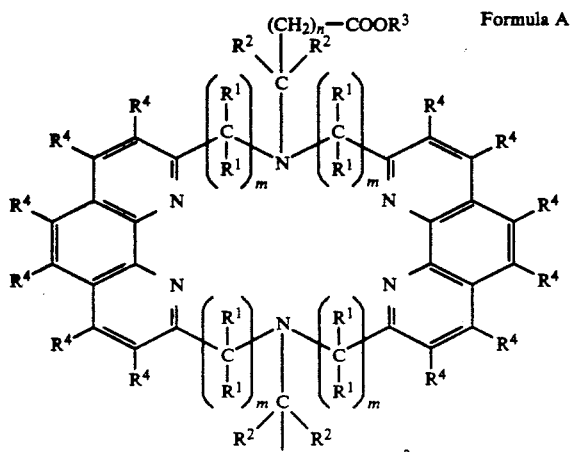

Formula A wherein m represents 1 or 2, n represents an integer selected from the group consisting of 0, 1, 2, 3 and 4;

$R^1$ is independently selected from the group consisting of hydrogen atom, an alkyl group, an alkenyl group, an alkynyl group, an aralkyl group, and an aryl group having carbon atoms up to 14;

$R^2$ is independently selected from the group consisting of hydrogen atom, an aryl group having carbon atoms up to 14, and an alkyl group;

$R^3$ is a functional group represented by $—R^{3-1}—R^{3-2}$, wherein $R^{3-1}$, although its presence is not indispensable, is independently selected from the group consisting of an alkylene group, an arylene group having carbon atoms up to 14, and an aralkylene group, nd $R^{3-2}$ is indispensable and independently selected from the group consisting of hydrogen atom, an alkyl group, an aryl group having carbon atoms up to 14, carboxyl group, hydroxyl group, an alkoxyl group, an amino group, an amide group, sulfonamide group, sulfide group, sulfoxide group, sulfone group, a halogen atom, carbonyl group, and nitro group; and $R^4$ is independently selected from the group consisting of hydrogen atom, an alkyl group, an alkenyl group, an alkynyl group, an aryl group having carbon atoms up to 14, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group represented by $—R^{4-1}—R^{4-2}$, wherein $R^{4-1}$, although its presence is not indispensable, is independently selected from the group consisting of an alkylene group, an alkenylene group, an arylene group having carbon atoms up to 14, and an aralkylene group, and $R^{4-2}$ is indispensable and independently selected from functional groups:

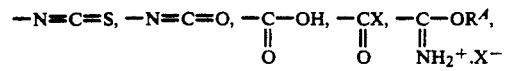

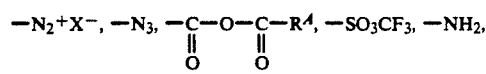

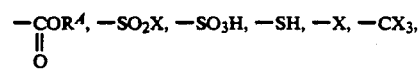

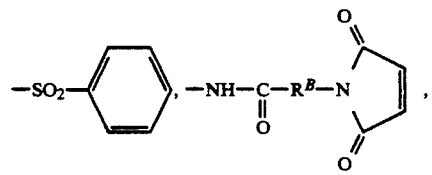

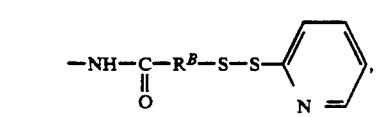

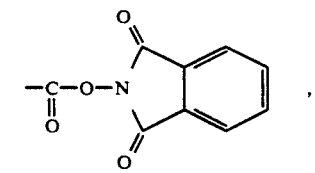

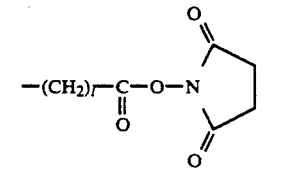

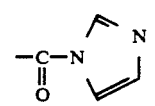

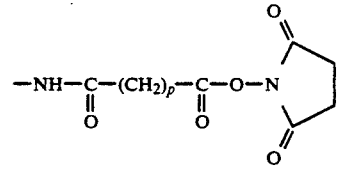

wherein X is selected from the group consisting of a halogen atom, $—OSO_3CH_3$, $—OSO_2F$, $—OSO_2CF_3$, $—SO_2C_4F_9$, and

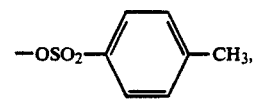

R is selected from the group consisting of an alkyl group, an alkenyl group, an aryl group having carbon atoms up to 14, and aralkyl group, $R^B$ is selected from the group consisting of an alkylene group, an alkenylene group, an arylene group having carbon atoms up to 14, and an aralkylene group, and l represents an integer of from 0 to 5, p represents an integer of from 2 to 10; and wherein, $R^4$ may optionally take a form of either at least one aromatic ring or at least one heterocyclic ring having N as heteroatom and aromatic 5 or 6 membered ring or fused ring thereof, when the heterocyclic ring has two or more N atoms, they are separated by one or two carbon atoms, wherein the heterocyclic ring includes two or three carbon atoms, which are the part of a phenanthroline ring as a result of the ring-forming condensation brought about by the bonding of neighboring $R^4$ to each other.

2. A fluorescent compound described in claim 1, which is expressed by formula B:

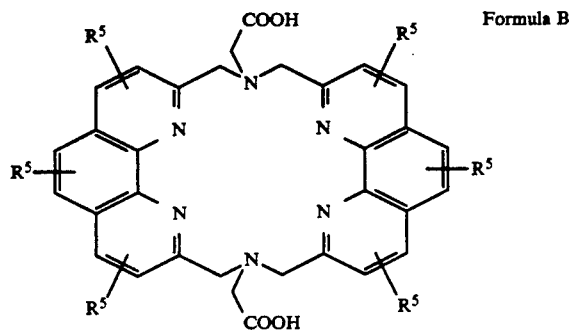

Formula B wherein $R^5$ is independently selected from the group consisting of hydrogen atom, an alkyl group, an alkenyl group, an alkynyl group, an aryl group having carbon atoms up to 14, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group represented by —$R^{5-1}$—$R^{5-2}$ (as defined above for —$R^{4-1}$—$R^{4-2}$).

3. A fluorescent compound according to claim 1, which are represented by formula C:

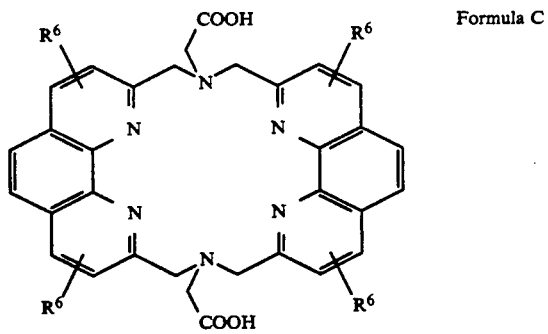

Formula C wherein $R^6$ is independently selected from a functional group represented by formula D:

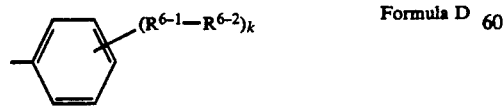

Formula D wherein —$R^{6-1}$—$R^{6-2}$ is as defined above for —$R^{4-1}$—$R^{4-2}$ and k represents an integer of from 0 to 5.

4. A fluorescent compound according to claim 1 wherein $R^3$ is

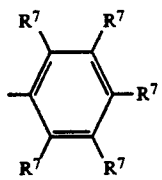

and $R^7$ is independently selected from the group consisting of hydrogen atom, an alkyl group, an alkenyl group, an alkynyl group, an aryl group having carbon atoms up to 14, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group expressed by —$R^{7-1}$—$R^{7-2}$, wherein —$R^{7-1}$—$R^{7-2}$ is defined in the same manner as for —$R^{4-1}$—$R^{4-2}$ in formula A.

5. A fluorescent compound according to claim 1 wherein $R^3$ is

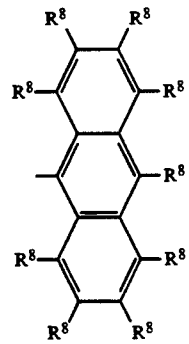

and $R^8$ is independently selected from the group consisting of hydrogen atom, an alkyl group, an alkenyl group, an alkynyl group, an aryl group having carbon atoms up to 14, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group expressed by —$R^{8-1}$—$R^{8-2}$, wherein —$R^{8-1}$—$R^{8-2}$ is defined in the same manner as for —$R^{4-1}$—$R^{4-13\ 2}$ in formula A.

6. A fluorescent compound according to claim 1 wherein $R^4$ is

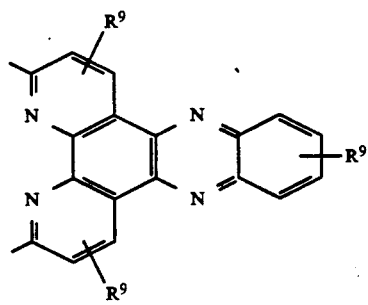

and $R^9$ is independently selected from the group consisting of hydrogen atom, an alkyl group, an alkenyl group, an alkynyl group, an aryl group having carbon atoms up to 14, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group expressed by —$R^{9-1}$—$R^{9-2}$, wherein —$R^{9-1}$—$R^{9-2}$ is defined in the same manner as for —$R^{4-1}$—$R^{4-2}$ in formula A.

7. A fluorescent compound according to claim 1 wherein $R^4$ is

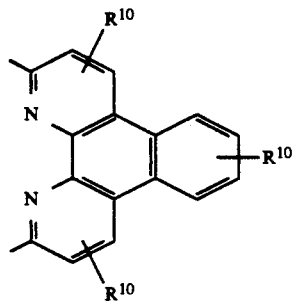

and $R^{10}$ is independently selected from the group consisting of hydrogen atom, an alkyl group, an alkenyl group, an alkynyl group, an aryl group having carbon atoms up to 14 which is substituted or unsubstituted, carboxyl group, hydroxyl group, an alkoxyl group, an amino group, an amide group, sulfonamide group, sulfide group, sulfoxide group, sulfone group, nitro group, a halogen atom, mercapto group, carbonyl group, and a functional group expressed by —$R^{10-1}$—$R^{10-2}$, wherein —$R^{10-1}$—$R^{10-2}$ is defined in the same manner as for —$R^{4-1}$—$R^{4-2}$ in formula A.

8. A fluorescent compound according to claim 1 wherein $R^4$ is expressed by —$R^{4-1}$—$R^{4-2}$, and $R^{4-2}$ is selected from a group consisting of —$SO_2Cl$, —$N=C=S$, —COOH and maleimide group.

9. The compound 2,15-diaza[3,3](2,9)-1,10-phenanthrolinophane-$N^2,N^{15}$-diacetic acid.

10. The compound 8-(3'-succinimidyloxycarbonyl-propionamide-2,15-diaza[3,3](2,9)-1,10-phenanthrolinophane-$N^2,N^{15}$-diacetic acid.

11. The compound 7,10-diphenyl-2,15-diaza[3,3](2,9)-1,10-phenanthrolinophane-$N^2,N^{15}$-diacetic acid.

12. The compound 7,10-bis(chlorosulfophenyl)-2,15-diaza(3,3](2,9)-1,10-phenanthrolinophane-$N^2,N^{15}$-diacetic acid.

13. The compound 7,10,20,23-tetrakis(chlorosulfophenyl)-2,15-diaza[3,3](2,9)-1,10-phenanthrolinophane-$N^2,N^{15}$-diacetic acid.

* * * * *